United States Patent
Wood et al.

(10) Patent No.: US 6,495,676 B1
(45) Date of Patent: *Dec. 17, 2002

(54) NUCLEIC ACID SEQUENCE DETECTION EMPLOYING PROBES COMPRISING NON-NUCLEOSIDIC COUMARIN DERIVATIVES AS POLYNUCLEOTIDE-CROSSLINKING AGENTS

(75) Inventors: Michael L. Wood, Mountain View, CA (US); David Albagli, Millbrae, CA (US); Reuel B. Van Atta, Mountain View, CA (US); Douglas Y. Thien, Menlo Park, CA (US); Peter C. Cheng, San Jose, CA (US); Bingfang Huan, Cupertino, CA (US)

(73) Assignee: Naxcor, Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/390,124

(22) Filed: Sep. 3, 1999

Related U.S. Application Data

(63) Continuation-in-part of application No. 09/149,161, filed on Sep. 4, 1998, now Pat. No. 6,277,570, which is a continuation-in-part of application No. 08/577,121, filed on Dec. 22, 1995, now Pat. No. 6,004,513, which is a continuation-in-part of application No. 08/487,034, filed on Jun. 7, 1995, now Pat. No. 5,676,259, which is a continuation-in-part of application No. 08/401,630, filed on Mar. 9, 1995, now Pat. No. 6,005,093, which is a continuation-in-part of application No. 08/364,339, filed on Dec. 27, 1994, now Pat. No. 5,616,464, which is a continuation-in-part of application No. 08/046,568, filed on Apr. 13, 1993, now abandoned.

(51) Int. Cl.$^7$ .............................................. C07H 21/00
(52) U.S. Cl. ................ 536/25.3; 536/25.31; 536/25.37; 435/6
(58) Field of Search ............................. 435/6; 536/25.3, 536/25.31, 25.32

(56) References Cited

U.S. PATENT DOCUMENTS

| | | | |
|---|---|---|---|
| 4,196,281 A | * 4/1980 | Hearst et al. ............... 536/24.5 |
| 4,378,458 A | * 3/1983 | Gohlke et al. ............. 536/24.3 |
| 4,582,789 A | 4/1986 | Sheldon, III et al. ........... 435/6 |
| 4,617,261 A | * 10/1986 | Sheldon, III et al. ........... 435/6 |
| 4,705,886 A | 11/1987 | Levenson et al. ........... 560/159 |
| 4,713,326 A | * 12/1987 | Dattagupta et al. ............. 435/6 |
| 4,737,454 A | * 4/1988 | Dattagupta et al. ............. 435/6 |
| 4,749,647 A | * 6/1988 | Thomas et al. ................ 435/6 |
| 4,751,313 A | 6/1988 | Levenson et al. ........... 548/303 |
| 4,754,065 A | 6/1988 | Levenson et al. ........... 562/564 |
| 4,820,630 A | 4/1989 | Taub ........................... 436/5 |
| 4,822,731 A | * 4/1989 | Watson et al. ................. 435/6 |
| 4,826,967 A | * 5/1989 | Glass ........................ 536/28.5 |
| 4,851,330 A | 7/1989 | Kohne ......................... 435/6 |
| 4,883,750 A | 11/1989 | Whiteley et al. ........... 435/803 |
| 4,965,188 A | 10/1990 | Mullis et al. .................. 435/6 |
| 5,026,840 A | * 6/1991 | Dattagupta et al. ...... 536/25.32 |
| 5,082,934 A | * 1/1992 | Saba et al. ................. 536/17.6 |
| 5,112,963 A | * 5/1992 | Pieles et al. ............... 536/24.3 |
| 5,118,801 A | 6/1992 | Lizardi et al. ................. 536/27 |
| 5,124,246 A | * 6/1992 | Urdea et al. ................... 435/6 |
| 5,139,940 A | 8/1992 | Isaacs et al. .................. 435/91 |
| 5,185,243 A | 2/1993 | Ullman ......................... 435/6 |
| 5,230,781 A | 7/1993 | Middendorf et al. ..... 204/182.8 |
| 5,270,183 A | 12/1993 | Corbett .................... 435/91.2 |
| 5,302,347 A | 4/1994 | van den Berg et al. ........ 422/67 |
| 5,312,728 A | 5/1994 | Lizardi et al. ................. 435/6 |
| 5,333,675 A | 8/1994 | Mullis et al. ................ 165/12 |
| 5,366,603 A | 11/1994 | Middendorf et al. ..... 204/182.8 |
| 5,424,413 A | 6/1995 | Hogan et al. ............. 436/24.31 |
| 5,449,602 A | 9/1995 | Royer et al. ................... 435/6 |
| 5,451,503 A | 9/1995 | Hogan et al. ................. 535/6 |
| 5,475,610 A | 12/1995 | Atwood et al. ............. 364/500 |
| 5,602,756 A | 2/1997 | Atwood et al. ............. 364/500 |
| 5,616,301 A | 4/1997 | Moser et al. ................ 422/104 |
| 5,629,149 A | 5/1997 | Santamaria et al. ............ 435/6 |
| 6,005,093 A | * 12/1999 | Wood et al. ............... 536/24.3 |

FOREIGN PATENT DOCUMENTS

| | | |
|---|---|---|
| DE | 4114482 | * 11/1992 |
| EP | 0 097 373 | 1/1984 |
| EP | 0 320 308 | 6/1989 |
| EP | 0 324 616 | 7/1989 |
| EP | 0 336 731 | 10/1989 |
| FR | 2642074 | * 7/1990 |
| JP | 1254855 | * 11/1986 |
| WO | 90/01069 | 2/1990 |
| WO | 9008156 | * 7/1990 |
| WO | 9012020 | * 11/1990 |
| WO | 9213629 | * 8/1992 |
| WO | 94/29485 | 12/1994 |

OTHER PUBLICATIONS

US 5,219,734, 6/1993, Royer et al. (withdrawn).

Ou et al.(I), "Photobinding of 8–Methoxypsoralens and 5,7–Dimethoxycoumarin to DNA and Its Effect on Template Activity," *Biochemistry*, 17(6), 1047–1053 (1978).*

Ou et al.(II), "Photobinding of 8–Methoxypsoralens to Transfer RNA and 5–Fluorouracil–Enriched Transfer RNA," *Biochemistry*, 17(6), 1054–1059 (1978).*

(List continued on next page.)

*Primary Examiner*—Deborah D. Carr
*Assistant Examiner*—Lawrence E. Crane
(74) *Attorney, Agent, or Firm*—Dorsey & Whitney LLP; Todd A. Lorenz

(57) ABSTRACT

Methods and compositions are provided for detecting nucleic acid sequences. Probes comprising a crosslinking agent are combined with a sample which may comprise a target sequence which is complementary to the probe. Hybridization is allowed to occur between complementary sequences. The crosslinking agent is activated. Covalent bonds are formed between the probe and the target sequence if they are hybridized to one another. The crosslinked nucleic acids can then be detected to indicate the presence of the target sequence. Also provided are kits comprising reagents.

24 Claims, 4 Drawing Sheets

OTHER PUBLICATIONS

Lown et al., "Photoreaction of Psoralen and Other Furocoumarins With Nucleic Acids," *Bioorg. Chem.*, 7(1), 85–95 (1978); *Chem. Abstr.*, 88, p. 259, Abstr. No. 184809s (1978); only Abstract provided.*

Seidel et al.(I), "Nucleic Acid Base Specific Quenching of a Coumarin–120–Derivative in Nucleotide–Conjugates–Photoinduced Electron Transfer?" *Proc. SPIE–Int. Soc. Opt. Eng., (Biomol. Spectrosc. 2*), 1991, 91–104.*

Seidel et al.(II), "Characterization of Fluorescence–Labeled DNA by Time Resolved Fluorescence Spectoscopy," *Proc. SPIE–Int. Soc. Opt. Eng., (Biomol. Spectrosc. 2*), 1991, 105–116.*

Alves, " A Chemical Method of Labeling Oligodeoxyribonucleotides with Biotin: A Single Step Procedure Using a Solid Phase Methodolgy," *Tetrahedron Letters*, 30(23), 3089–3092 (1989).*

Boiziau et al., "Mechanisms of the Inhibition of Reverse Transcriptase by Antisense Oligonucleotides," *Proc. Nat. Acad. Sci. USA*, 89, 768–772 (Jan. 1992).*

Cimino et al., "Psoralens as Photoactive Probes of Nucleic Acids Structure and Function: Organic Chemistry, Photochemistry, and Biochemistry," *Ann. Rev. Biochem.*, 54, 1151–1193 (1985).*

Cocuzza, "A Phosphoramidite Reagent for Automated Solid Phase Synthesis of 5'–Biotinylated Oligonucleotides," *Tetrahedron Letters*, 30(46), 6287–6290 (1989).*

Gamper et al., "Solution Hybridization of Crosslinkable DNA Oligonucleotides to Bacteriophage M13 DNA—Effect of Secondary Structure on Hybridization Kinetics and Equlibria," *J. Molecular Biology*, 197, 349–362 (1987).*

Goodchild, "Conjugates of Oligonucleotides and Modified Oligonucleotides: A Review of Their Synthesis and Properties," *Bioconjugate Chemistry*, 1(3), 165–187 (May/Jun. 1990).*

Haralambidis et al., "The Preparation of Polyamide–Oligonucleotide Probes Containing Multiple Non–radioactive Labels," *Nucleic Acids Research*, 18(3), 501–501 (1990).*

Lee et al., "Interaction of Psoralen–Derivatized Oligodeoxyribonucleoside Methylphosphonates with Single–Stranded DNA," *Biochemistry*, 27(9), 3197–3203 (1988).*

Misiura et al., "Biotinyl and Phosphotyrosinyl Phosphoramidite Derivatives Useful in the Incorporation of Multiple Reported Groups on Synthetic Oligonucleotides," *Nucleic Acids Research*, 18(15), 4345–4354 (1990).*

Nelson et al.(I), "A New and Versatile Reagent for Incorporating Multiple Primary Aliphatic Amines into Synthetic Oligonucleotides," *Nucleic Acids Research*, 17(18), 7179–7186 (1989).*

Nelson et al.(II), "Bifunctional Oligonucleotide Probes Synthesized Using a Novel CPG Support Are Able to Detect Single Base Pair Mutations," *Nucleic Acids Research*, 17(18), 7187–7194 (1989).*

Nelson et al.(III), "Oligonucleotide Labelling Methods. 3. Direct Labeling of Oligonucleotides Employing a Novel, Non–Nucleosidic, 2–Amino–1,3–propanediol Backbone," *Nucleic Acids Research*, 20(23), 6253–6259 (1992).*

Pieles et al.(I), "Psoralen Covalently Linked to Oligodeoxyribonucleotides: Synthesis, Sequence Specific Recognition of DNA and Photo–Cross–Linking to Pyrimidine Residues of DNA," *Nucleic Acids Research*, 17(1), 285–299 (1989).*

Pieles et al.(II), "Preparation of a Novel Psoralen Containing Deoxyadenosine Building Block for the Facile Solid Phase Synthesis of Psoralen–Modified Oligonucleotides for a Sequence–Specific Crosslink or a Given Target Sequence," *Nucleic Acids Research*, 17(22), 8967–8978 (1989).*

Takasugi et al., "Sequence–Specific Photo–Induced Cross–Linking of the Two Strands of Double–Helical DNA by a Psoralen Covalently Linked to a Triple Helix–Forming Oligonucleotide," *Proc. Nat. Acad. Sci. USA*, 88, 5602–5606 (Jul. 1991).*

Suortti et al., "Necatorin, A Highly Mutagenic Compound from *Lactarius Necator,*" *Phytochemistry*, 22(12), 2873–2874 (1983).*

Lown et al., "Photoreaction of Psoralen and Other Furocoumarins with Nucleic Acids," *Bioorganic Chemistry*, 7(1), 85–95 (1978).*

Seidel, "Nucleic Acid Base Specific Quenching of a Coumarin–120–Derivative in Nucleotide–Conjugates—Photoinduced Electron Transfer?" presented Jan. 22–23, 1991, "Biomolecular Spectroscopy II," Birge et al. (eds.), SPIE Meeting, Los Angeles, CA, published in *Proceedings of the SPIE*, 1432, 91–104 (1991).*

Seidel, "Nucleic Acid Base Specific Quenching of a Coumarin–120–Derivative in Nucleotide–Conjugates—Photoinduced Electron Transfer?" presented Jan. 22–23, 1991, "Biomolecular Spectroscopy II," Birge et al. (eds.), SPIE Meeting, Los Angeles, CA, published in *Proceedings of the SPIE*, 1432, 91–104 (1991).*

Seidel et al., "Characterization of Fluorescence–Labelled DNA by Time–Resolved Fluorescence Spectroscopy," presented Jan. 22–23, 1991, "Biomolecular Spectroscopy II," Birge et al. (eds.), SPIE Meeting, Los Angeles, CA, published in *Proceedings of the SPIE*, 1432, 105–116 (1991).*

Guatelli et al., "Isothermal, In Vitro Amplification of Nucleic Acids by a Multienzyme Reaction Modeled After Retroviral Replication," *PNAS*, 87:1874–1878 (1990). (Mar., 1990).

Barany, "Genetic Disease Detection and DNA Amplification Using Cloned Thermostable Ligase," *PNAS*, 88:189–193 (1991), (Jan. 1, 1991).

Nilsson et al., "Padlock Probes: Circularizing Oligonucleotides for Localized DNA Detection," *Science*, 265:2085–2088 (1994). (Sep. 30, 1994).

Wood et al., "Nucleic Acid Crosslinking Probes for DNA/RNA Diagnostics," Presented at the Annual meeting of the American Association for Clinical Chemistry & the Canadian Society of Clinical Chemists Jul. 28–Aug. 1, 1996, Chicago, IL. p. 1–5.

Zehnder, J., "Cross–Linking Hybridization Assay for Direct Detection Factor V Leiden Mutation," *Clinical Chemistry*, 43:9, 1703–1708 (1997).

* cited by examiner

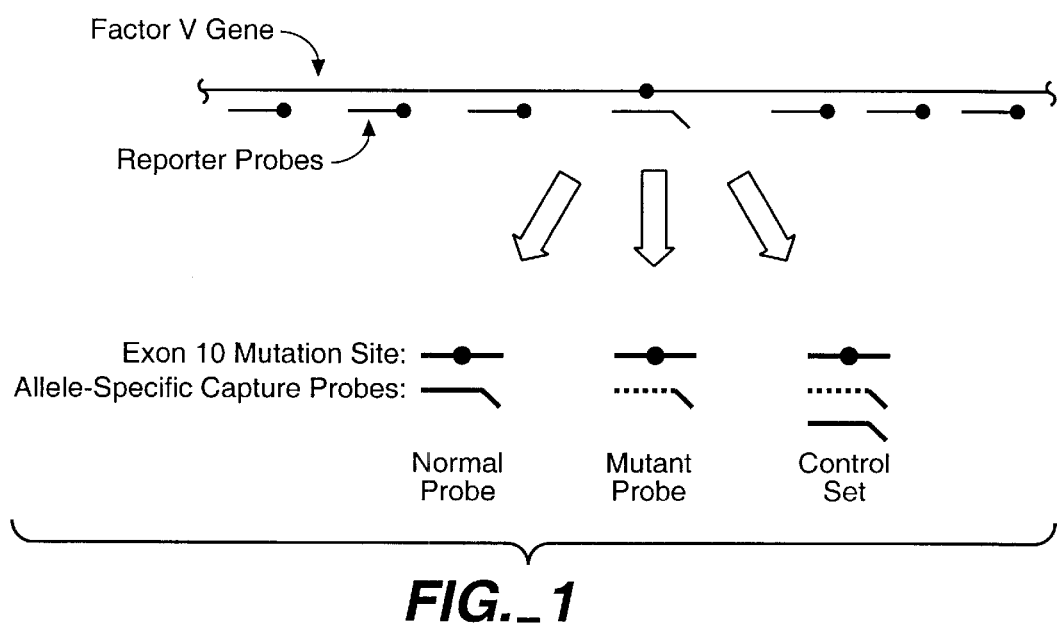
FIG._1

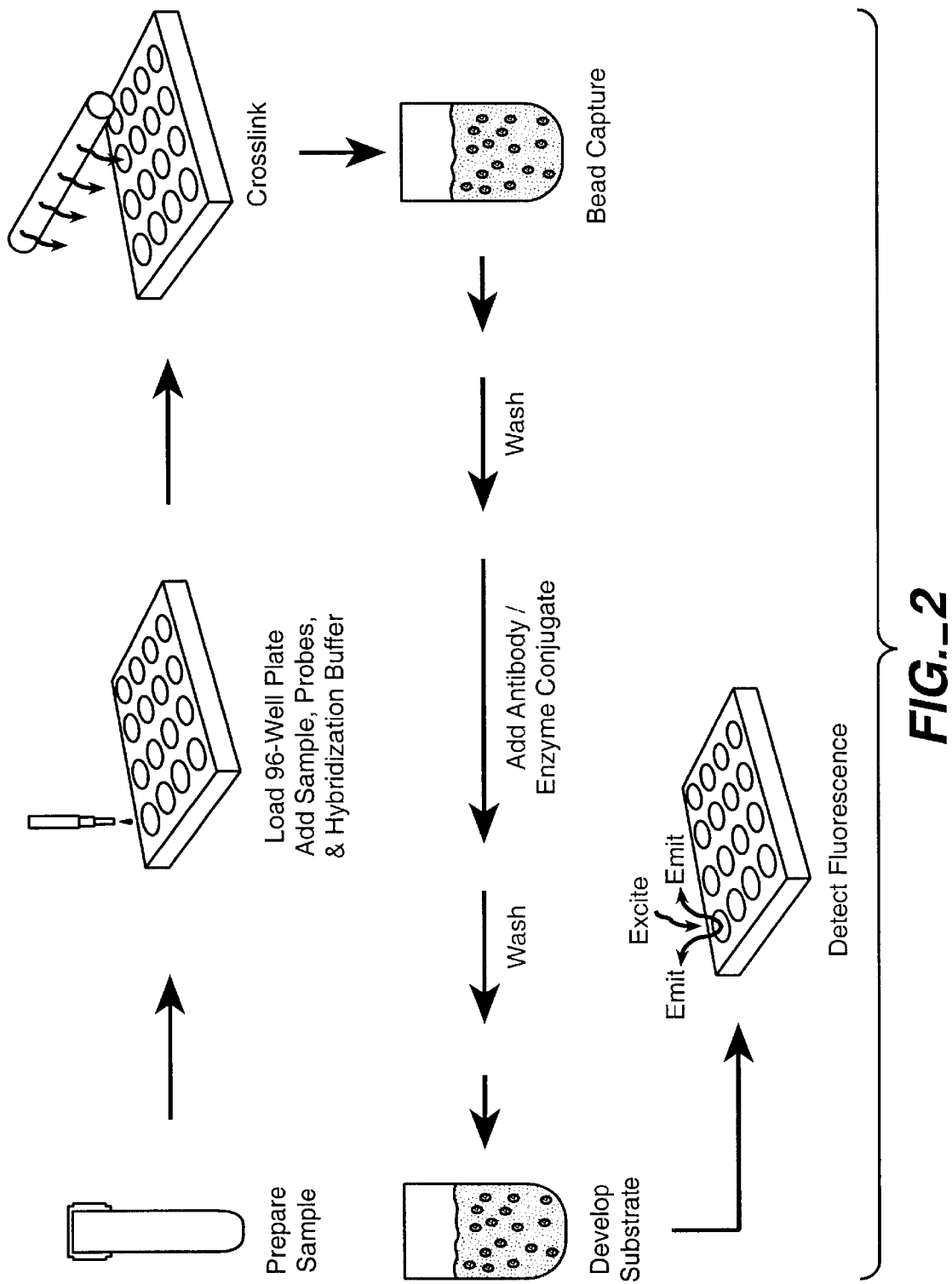
FIG._2

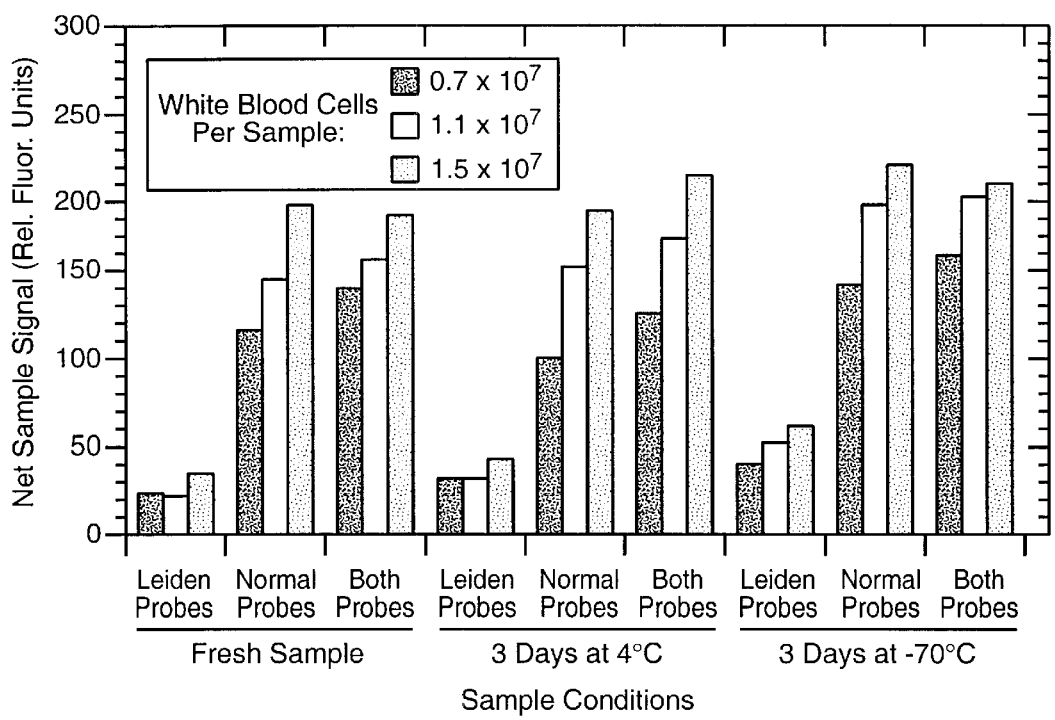
FIG._3
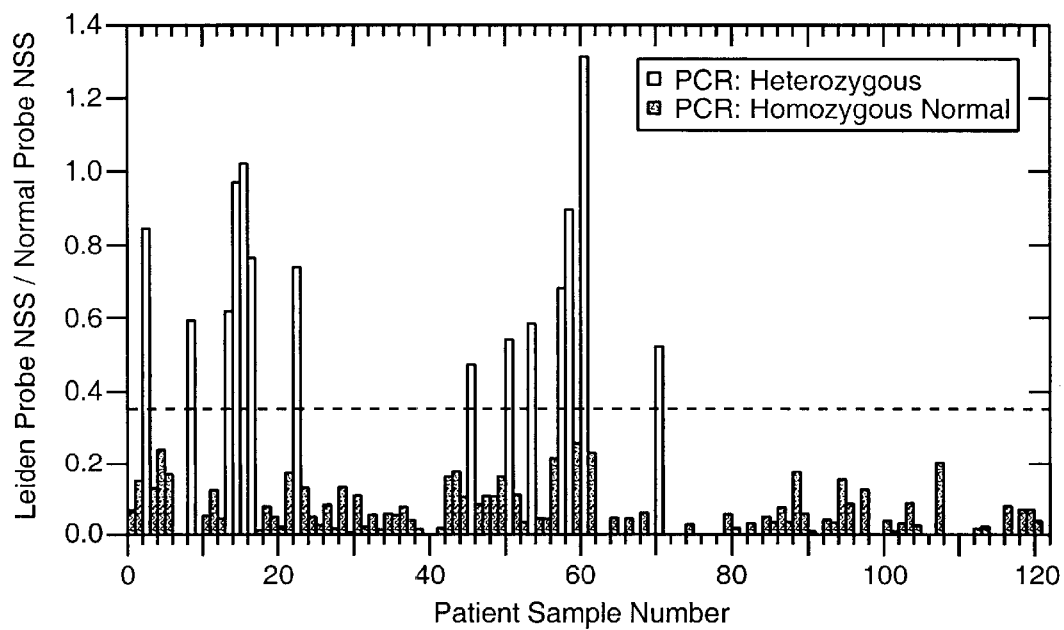
FIG._4

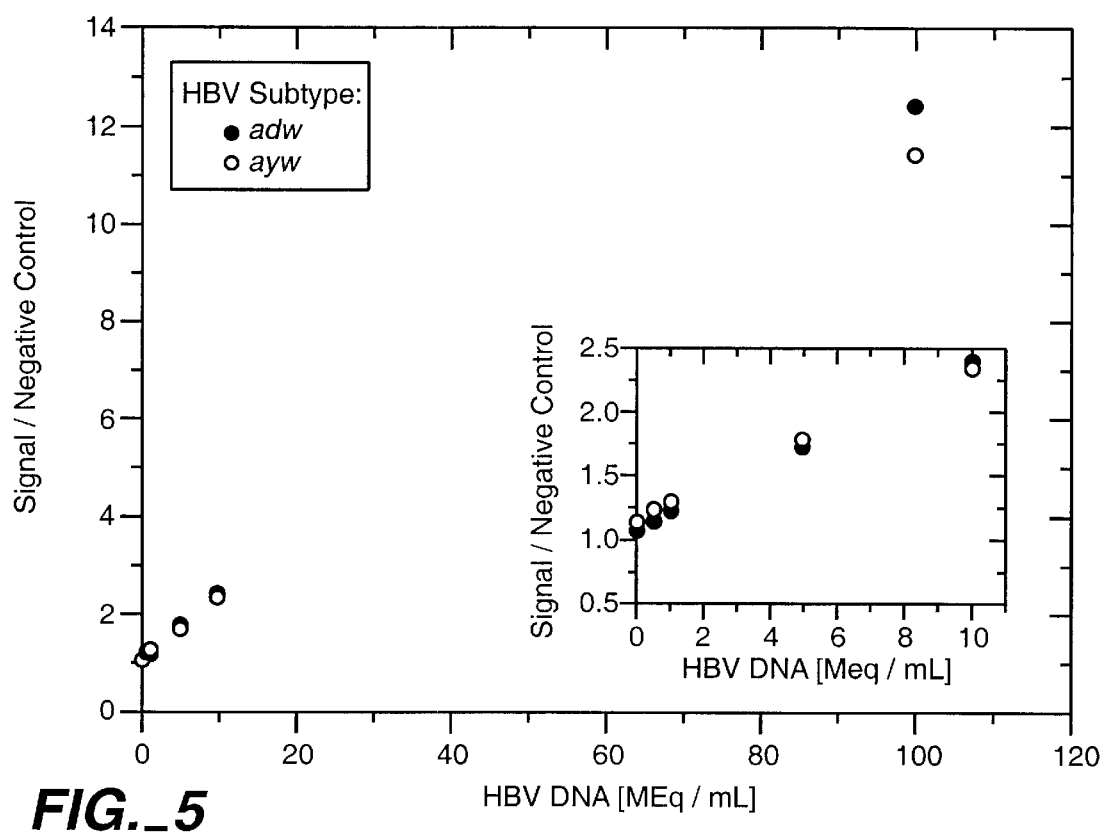
FIG._5
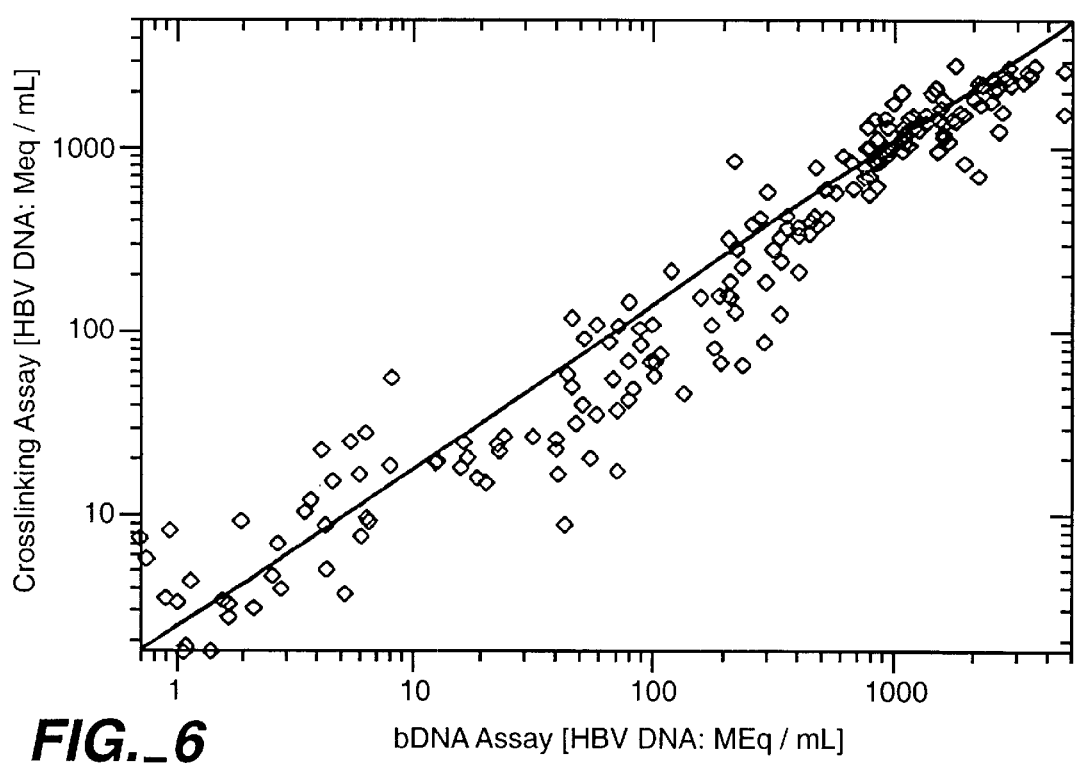
FIG._6

SEQUENCE LISTING

```
<160> NUMBER OF SEQ ID NOS: 19

<210> SEQ ID NO 1
<211> LENGTH: 25
<212> TYPE: DNA
<213> ORGANISM: Probe for Hepatitis B virus

<400> SEQUENCE: 1
gtttttcttg ttgaacaaaa atcct                           25

<210> SEQ ID NO 2
<211> LENGTH: 26
<212> TYPE: DNA
<213> ORGANISM: Probe for Hepatitis B virus

<400> SEQUENCE: 2
tttctagggg gaacacccgt gtgtct                          26

<210> SEQ ID NO 3
<211> LENGTH: 60
<212> TYPE: DNA
<213> ORGANISM: Probe for Hepatitis delta, viral origin

<400> SEQUENCE: 3
ctgggaaaca tcaaaggaat tctcggaaag aaagccagca gtctcctctt tacagaaaag    60

<210> SEQ ID NO 4
<211> LENGTH: 26
<212> TYPE: DNA
```

```
<213> ORGANISM: Probe for Vancomycin resistance, generally bacterial
      origin

<400> SEQUENCE: 4
cataggggat accagacaat tcaaac                                             26

<210> SEQ ID NO 5
<211> LENGTH: 25
<212> TYPE: DNA
<213> ORGANISM: Probe for Vancomycin resistance, generally bacterial
      origin

<400> SEQUENCE: 5
acctgaccgt gcgcccttca caaag                                              25

<210> SEQ ID NO 6
<211> LENGTH: 25
<212> TYPE: DNA
<213> ORGANISM: Probe for Vancomycin resistance, generally bacterial
      origin

<400> SEQUENCE: 6
acgatgccgc catcctcctg caaaa                                              25

<210> SEQ ID NO 7
<211> LENGTH: 26
<212> TYPE: DNA
<213> ORGANISM: Probe for Vancomycin resistance, generally bacterial
      origin

<400> SEQUENCE: 7
cacagaccat tcgcagtatt gaaaac                                             26

<210> SEQ ID NO 8
<211> LENGTH: 14
<212> TYPE: DNA
<213> ORGANISM: Probe for factor V gene
<220> FEATURE:
<223> OTHER INFORMATION: T-crosslinker attached at 5' end.

<400> SEQUENCE: 8
ttcctcgcct gtcc                                                          14

<210> SEQ ID NO 9
<211> LENGTH: 14
<212> TYPE: DNA
<213> ORGANISM: Probe for the presence of Chlamydia trachomatis.
<220> FEATURE:
<223> OTHER INFORMATION: T-crosslinker attached at 5' end.

<400> SEQUENCE: 9
ttccttgcct gtcc                                                          14

<210> SEQ ID NO 10
<211> LENGTH: 17
<212> TYPE: DNA
<213> ORGANISM: Probe for the presence of Chlamydia trachomatis.
<220> FEATURE:
<223> OTHER INFORMATION: 7-coumarinyl glycero-AATT attached at 3' end.

<400> SEQUENCE: 10
agttaatccc agacgca                                                       17

<210> SEQ ID NO 11
<211> LENGTH: 17
```

```
<212> TYPE: DNA
<213> ORGANISM: Probe for the presence of Chlamydia trachomatis.
<220> FEATURE:
<223> OTHER INFORMATION: 7-coumarinyl glycerol attached at 5' end.
<223> OTHER INFORMATION: 7-coumarinyl glycerol-AATT-biotin attached
      at 3' end.

<400> SEQUENCE: 11
agttaatccc agacgca                                                        17

<210> SEQ ID NO 12
<211> LENGTH: 25
<212> TYPE: DNA
<213> ORGANISM: Probe for the presence of Chlamydia trachomatis.
<220> FEATURE:
<223> OTHER INFORMATION: 7-coumarinyl glycerol attached at 5' end.
<223> OTHER INFORMATION: 7-coumarinyl glycerol-AT attached at 3' end.

<400> SEQUENCE: 12 agaagattt cgttatagga ggaca                                                25

<210> SEQ ID NO 13
<211> LENGTH: 25
<212> TYPE: DNA
<213> ORGANISM: Probe for the presence of Chlamydia trachomatis.
<220> FEATURE:
<223> OTHER INFORMATION: 7-coumarinyl glycerol attached at 5' end.
<223> OTHER INFORMATION: 7-coumarinyl glycerol-AT-biotin attached at 3'
      end.

<400> SEQUENCE: 13
agaagatttt cgttatagga ggaca                                               25

<210> SEQ ID NO 14
<211> LENGTH: 25
<212> TYPE: DNA
<213> ORGANISM: Probe for the presence of Chlamydia trachomatis.
<220> FEATURE:
<223> OTHER INFORMATION: 7-coumarinyl glycerol attached at  5' end.
<223> OTHER INFORMATION: 7-coumarinyl glycerol attached at 3' end.

<400> SEQUENCE: 14
atttggttat ctactttatc ttatc                                               25

<210> SEQ ID NO 15
<211> LENGTH: 25
<212> TYPE: DNA
<213> ORGANISM: Probe for the presence of Chlamydia trachomatis.
<220> FEATURE:
<223> OTHER INFORMATION: 7-coumarinyl glycerol attached at 5' end.
<223> OTHER INFORMATION: 7-coumarinyl glycerol-AT-biotin attached at 3'
      end.

<400> SEQUENCE: 15
agaagatttt cgttatagga ggaca                                               25

<210> SEQ ID NO 16
<211> LENGTH: 19
<212> TYPE: DNA
<213> ORGANISM: Probe for the presence of Chlamydia trachomatis.
<220> FEATURE:
<223> OTHER INFORMATION: fluorescein- glycerol (symmetric branch)
      attached at 5' end.
<223> OTHER INFORMATION: 7-coumarinyl glycerol-AT attached at 3' end.

<400> SEQUENCE: 16
tctaccacca agagttgca                                                      19
```

```
<210> SEQ ID NO 17
<211> LENGTH: 24
<212> TYPE: DNA
<213> ORGANISM: Probe for the presence of Chlamydia trachomatis.
<220> FEATURE:
<223> OTHER INFORMATION: fluorescein-glycerol-glycerol (summetric
      branch)-A- 7-coumarinyl glycerol attached at 5'
      end.
<223> OTHER INFORMATION: 7-coumarinyl glycerol-AT attached at 3' end.

<400> SEQUENCE: 17
agctcgtaat atgcaagagc attg                                          24

<210> SEQ ID NO 18
<211> LENGTH: 23
<212> TYPE: DNA
<213> ORGANISM: Probe for the presence of Chlamydia trachomatis.
<220> FEATURE:
<223> OTHER INFORMATION: fluorescein- glycerol-glycerol (symmetric
      branch)-A- 7-coumarinyl glycerol attached at 5'
      end.
<223> OTHER INFORMATION: 7-coumarinyl glycerol-AT attached at 3' end.

<400> SEQUENCE: 18
aattcactat ccggagcgct tca                                           23

<210> SEQ ID NO 19
<211> LENGTH: 20
<212> TYPE: DNA
<213> ORGANISM: Probe for the presence of Chlamydia trachomatis.
<220> FEATURE:
<223> OTHER INFORMATION: fluorescein- glycerol-glycerol (symmetric
      branch)-G- 7-coumarinyl glycerol attached at 5'
      end.

<400> SEQUENCE: 19
agactttgca actcttggtg                                               20
```

NUCLEIC ACID SEQUENCE DETECTION EMPLOYING PROBES COMPRISING NON-NUCLEOSIDIC COUMARIN DERIVATIVES AS POLYNUCLEOTIDE-CROSSLINKING AGENTS

CROSS REFERENCE TO RELATED APPLICATION

This application is a continuation-in-part of U.S. application Ser. No. 09/149,161, filed on Sep. 4, 1998, now U.S. Pat. No. 6,277,570, which is a continuation-in-part of U.S. application Ser. No. 08/577,121, filed on Dec. 22, 1995, now U.S. Pat. No. 6,004,513, which is a continuation-in-part of U.S. application Ser. No. 08/487,034, filed on Jun. 7, 1995, now U.S. Pat. No. 5,676,259, which is a continuation-in-part of U.S. application Ser. No. 08/401,630, filed on Mar. 9, 1995, now U.S. Pat. No. 6,005,093, which is a continuation-in-part of U.S. application Ser. No. 08/364,339, filed on Dec. 27, 1994, now U.S. Pat. No. 5,616,464, which is a continuation-in-part of U.S. application Ser. No. 08/046,568, filed on Apr. 13, 1993, now abandoned.

TECHNICAL FIELD

The field of this invention is nucleic acid sequence detection. The invention employs probes comprising photoactive analogues that can be incorporated into synthetic oligonucleotides during automated DNA synthesis for use in crosslinking of complementary nucleic acid sequences.

BACKGROUND

The amount of information concerning the genomes of a large variety of species is increasing exponentially. The availability of known sequences creates an enormous market for the detection of particular sequences present as DNA or RNA, whereby one can detect the presence of genes, their transcription products, polymorphic sequences, or mutations, such as lesions, substitutions, deletions, translocations, and the like. By knowing sequences of interest, one can detect a wide variety of pathogens, particularly unicellular microorganisms and viral strains, and genetic diseases including the presence of genes imparting antibiotic resistance to the unicellular microorganisms, as illustrative of only a few of the available possibilities. In addition, there are needs within the extensive areas of genetic counseling, forensic medicine, research, regulatory inspection of genetically modified organisms, and the like, for nucleic acid sequence detection technology.

In many instances, the target nucleic acid sequence is only a very small proportion of total nucleic acid in the sample. Furthermore, there may be many situations where the target nucleic acid of interest and other sequences present have substantial homology. It is therefore important to develop methods for the detection of the target nucleic acid sequence that are both sensitive and accurate.

Furthermore, oligonucleotide probe-based assay methods are known to depend upon careful optimization of the wash stringency. If the wash conditions are too stringent, then probe/target hybrids will be denatured, resulting in a decrease in the amount of signal in the assay. If the wash conditions are not sufficiently stringent, then non-specifically bound probes or mismatched probe/target hybrids will remain in the assay medium, resulting in high levels of non-specific or background signal in the assay. Optimal conditions are necessarily different for each probe because hybridization is a sequence-dependent phenomenon and would also depend on the extent to which near-homologous sequences are present in the sample.

The use of crosslinkable probes in nucleic acid hybridization assays to crosslink to target sequences is demonstrated in U.S. Pat. No. 4,826,967 by K. Yabusaki et al.; compounds are based on furocoumarin, (or psoralen) attached to existing polynucleotides (usually through adduct formation) and are satisfactory for many applications. However the crosslinking group/nucleoside adduct is difficult to synthesize particularly in large quantities. In U.S. Pat. No. 5,082,934, Saba et al. describe a photoactivatible nucleoside analogue comprising a coumarin moiety linked through its phenyl ring to the 1-position of a ribose or deoxyribose sugar moiety in the absence of an intervening base moiety. The resulting nucleoside analogue is used as a photo-crosslinking group when inserted into a polynucleotide as a replacement for one or more of the complementary nucleoside bases present in a probe used in hybridization assays. Nevertheless, new types of compounds that offer additional advantages, such as stability throughout probe synthesis and use, and conformational flexibility, continue to remain desirable.

There is, therefore, substantial interest in identifying alternative techniques which allow for the detection of specific DNA sequences and avoid the deficiencies of the other systems.

SUMMARY OF THE INVENTION

This invention provides non-nucleosidic, stable, photoactive compounds that can be used as photo-crosslinking reagents in nucleic acid hybridization assays, which may include genotyping and mutation detection assays, as well as techniques and intermediates that can be used to prepare the final products.

The compounds comprise coumarinyl derivatives prepared by linking the phenyl ring of a coumarin molecule or derivative to a hydroxy or polyhydroxy hydrocarbon molecule, such as one of the terminal hydroxy groups of a glycerol molecule. The (poly)hydroxy hydrocarbon moiety of the resulting compound is equivalent to the sugar of a nucleoside, while the coumarin moiety occupies the position of a base. It is to be understood that the (poly)hydroxy hydrocarbon moiety of the resulting compound is other than ribose or deoxy ribose. Accordingly, the compounds can be inserted into growing polynucleotide chains using automated (or manual) techniques of polynucleotide synthesis. The double bond between the 3 and 4 positions of the coumarin ring system is a photoactive group that covalently crosslinks to nucleosides in the complementary strand when an oligonucleotide containing this non-nucleoside analogue (the "crosslinkable probe") is used in a hybridization assay and/or therapeutic application.

For the most part, the photoactive compound has the formula

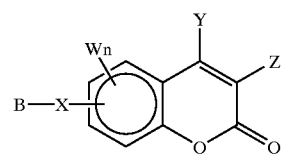

in which the substituents and linking groups are described below in more detail.

The (poly)hydroxy hydrocarbon backbones give maximum flexibility and stability to the oligonucleotide structure in which they are located as well as good solubility in aqueous and organic media.

Also provided herein are methods of use of the crosslinkable probe described herein. Methods and compositions are provided for detecting nucleic acid sequences by using the crosslinkable probe provided herein which comprises a cross linking system. Upon hybridization of the crosslinkable probe to the target and activation of the cross linking system, the crosslinkable probe and target are joined together by a covalent linkage. The method employs adding the crosslinkable probe to the target nucleic acid under conditions of base pairing and activating the crosslinking system, so that a covalent bond is formed between the target and the crosslinkable probe.

In a preferred embodiment, the crosslinkable probe includes a molecule that can be captured on a solid support, e.g., biotin, and thus can be captured on e.g., streptavidin-coated magnetic beads (a "capture probe"). In another preferred embodiment, one or more crosslinkable probes which also are complementary to the target nucleic acid sequence, include a reporter molecule, e.g., a fluorophore, an antigen, or other binding pair partner useful for direct or indirect detection methods (a "reporter probe").

BRIEF DESCRIPTION OF THE DRAWINGS

FIG. 1 is a schematic of an assay in accordance with the present invention.

FIG. 2 is a schematic of an assay in accordance with the present invention.

FIG. 3 is bar graph showing different sample conditions in relation to net sample signal (NSS) indicating the effect of sample storage and cell number on the performance of the factor V Leiden mutation assay performed herein.

FIG. 4 is a bar graph showing patient sample number in relation to NNS wherein NNS ratios were obtained from testing 122 individuals with an assay in accordance with the present invention.

FIG. 5 shows a standard response curve of an assay performed in accordance with the present invention to identify Hepatitis B viral DNA (HBV).

FIG. 6 shows the correlation between a quantitative HBV DNA assay provided herein versus a commercially available test assay.

DESCRIPTION OF THE SPECIFIC EMBODIMENTS

The present invention provides crosslinkable compounds that can be used as a photoactivatible non-nucleosidic crosslinker in oligonucleotide probes used in hybridization assays and/or therapeutic applications. The probes comprising the photoactivatible non-nucleosidic crosslinkers described herein are sometimes referred to herein as capture probes and/or reporter probes.

In hybridization assays, the crosslinkable probes of the inventions are typically used to determine the presence or absence of a specific DNA and RNA base sequence in a sample. More specifically, this invention provides capture probes comprising coumarin derivatives attached to a stable, flexible, (poly)hydroxy hydrocarbon backbone unit that act as photoactive crosslinking compounds in hybridization assays. Wherein the coumarin derivative is incorporated into the backbone of an oligonucleotide probe, as described below, so as to replace one or more nucleotides otherwise complementary to a target nucleic acid sequence, the coumarin moiety is referred to as a non-nucleosidic coumarin derivative.

The crosslinking compounds of the invention have the general formula:

Backbone moiety—Linking moiety—Crosslinking moiety

"Moiety" here and elsewhere in this specification indicates a part of a molecule that performs the indicated function. A given moiety is usually derived from another molecule by covalently linking together two or more molecules, with the identifiable remnants of the original molecules being referred to as "moieties." For example, if a psoralen molecule is attached to a glycerin molecule with a divalent linker, such as a methylene group, the resulting single molecule is referred to as being formed of glycerin, methylene, and psoralen moieties. It is not necessary, however, that the three moieties actually arose from three separate molecules, as discussed below. Thus "derived from" can refer to theoretical, as well as actual, precursors.

The crosslinking moiety will be derived from molecules having a fused benzopyrene structure, such as the following: (1) coumarin and its simple derivatives; (2) psoralen and its derivatives, such as 8-methoxypsoralen or 5-methoxypsoralen (at least 40 other naturally occurring psoralens have been described in the literature and are useful in practicing the present invention); (3) cis-benzodipyrone and its derivatives; (4) trans-benzodipyrone; and (5) compounds containing fused coumarin-cinnoline ring systems. All of these molecules contain the necessary crosslinking group (an activated double bond) located in the right orientation and at the right distance to crosslink with a nucleotide in the target strand. All of these molecules are coumarin derivatives, in that all contain the basic coumarin (benzopyrene) ring system on which the remainder of the molecule is based.

The linking moiety will normally be formed from a precursor that contains from 1 to 100, preferably 1 to 25, more preferably 1 to 10, atoms with functional groups at two locations for attaching the other moieties to each other. After reaction of the precursor to form the linking moiety, the total number of atoms in the shortest linking chain of atoms between the coumarin ring system and the backbone moiety (sugar substitute) is generally from 1 to 15, preferably 1 to 7, more preferably 1 to 3. Otherwise this part of the structure can vary widely, as this is essentially just a flexible linkage from the crosslinking moiety to the backbone moiety.

The linking moiety is most often a stable cyclic or acyclic moiety derived by reaction of a molecule bearing appropriate functional groups (usually at its termini) for linking the crosslinking molecule at one end and the backbone molecule at the other end. However, if sufficient functional groups are present in the backbone and crosslinking moieties, a precursor to the linking moiety need not be used (i.e., the backbone and crosslinking moieties can be connected by a covalent bond).

It should be recognized that description of a particular part of the final molecule as belonging to a particular moiety of those identified above is somewhat arbitrary and does not necessarily mean that there were three original molecules that reacted to form the final product. There are a number of coumarin derivatives, for example, that have a functionalized methyl or methoxy group attached to the coumarin ring that can react with a functional group on a backbone moiety precursor to form a product from only two starting materials. However, the resulting structure will generally appear to have three parts as indicated above: the backbone molecule that is incorporated into the sugar backbone of a polynucleotide, the crosslinking moiety that occupies the space occupied by a base in a normal nucleoside, and the atoms (i.e., the linking moiety) that join the two principal parts together. For the sake of convenience, the linking moiety is considered to consist of atoms between the ring atom of the crosslinking moiety at the point of attachment and the last carbon atom that clearly forms part of the backbone structure in the moiety that replaces the sugar molecule, which is usually the carbon atom bearing a hydroxyl group (or reaction product of a hydroxyl group) that is closest to the crosslinking moiety.

The backbone moiety, so called because it ultimately functions in place of the ribose or deoxyribose portion of the backbone of a polynucleotide, will generally have 1 to 3 (sometimes more) hydroxyl groups (or similar functional groups, as discussed below) attached to different $sp^3$-hybridized carbon atoms. The backbone moiety is generally uncharged so that it can function as a substitute for ribose or deoxyribose in the final modified nucleotide. Backbone moieties include but are not limited to the following: (1) linear hydrocarbon moieties such as a three-carbon propane unit or a longer hydrocarbon chain with appropriate functional groups, usually selected from the group consisting of —OH, —NH$_2$, —SH, —COOH, acid halides, and acid anhydrides, and (2) cyclic hydrocarbon moieties typically having a 5- to 7-membered carbon ring structure bearing one to three hydroxyl group or other functional groups as in (1) above. The functional groups are shown in the preceding sentence in unreacted form and will be present as derivatives of the indicated functional groups in many embodiments. The reactive functional groups mentioned above (other than —OH and —SH) are generally present only in intermediates; however, after reacting with other functional groups, they become stable groups or form, covalent bonds to other parts of the molecule.

In addition to the basic structure described above, one or more coupling moieties can be attached to the backbone moiety to facilitate formation of bonds to existing or growing polynucleotide chains. The coupling moieties will typically comprise hydroxy coupling and/or protecting groups that are used in solution or solid-phase nucleic acid synthesis when the molecule in question is an intermediate being used in the preparation of a probe molecule. Typical coupling groups include phosphoramidite, phosphate, H-phosphonate, phosphorothioate, methyl phosphonate, trityl, dimethoxytrityl, monomethoxytrityl, and pixyl groups. Non-phosphorous coupling groups include carbamates, and amides.

Preferred compounds of the invention have the formula:

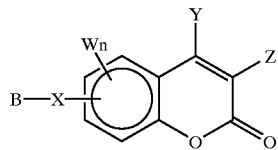

wherein
 B represents (1) a linear, branched, or cyclic hydrocarbon group containing from 2 to 15, preferably 3 to 10, more preferably 3 to 6, carbon atoms and, if cyclic, containing a 5- or 6-membered ring or (2) a heterocyclic aromatic ring system comprising a 5- or 6-membered ring, said B(1) or B(2) being substituted with 1, 2, or 3 groups of the formula OR$_1$;
 X represents (1) a bond, (2) a linear, branched, or cyclic hydrocarbon group containing 1 to 15, preferably 2 to 10, more preferably 3 to 6, carbon atoms or (3) such an X(2) group in which one to three (preferably one) carbon atom or atoms of the hydrocarbon group are replaced by an oxygen, sulfur, or nitrogen atom and in which the shortest linking chain of atoms in X between atoms in other parts of the formula attached to X is 1 to 10 atoms, wherein X is optionally substituted with 1–3 substituents selected from the group consisting of hydroxy, halogen, amino, amido, azido, carboxy, carbonyl, nitro, thio, perfluoromethyl, and cyano functional groups; and wherein X is attached to the phenyl ring of said formula directly or through W;
 n is 0, 1, 2, or 3;
 each W independently represents a hydroxy, halogen, amino, amido, azido, nitro, thio, carboxy, carbonyl, perfluoromethyl, or cyano functional group; an unsubstituted hydrocarbyl group of 10 or fewer carbon atoms, preferably 6 or fewer, more preferably 3 or fewer; or such a hydrocarbyl group substituted with 1–3 of the functional groups or in which one carbon atom is replaced by an oxygen, sulfur, or nitrogen atom; with the provisos that (1) when X or W is a substituted hydrocarbon, the total number of substituents in X or W is less than the total number of carbon atoms in the X or W and no more than one substituent or heteroatom is attached to a given carbon, unless the substituents are halogen atoms on the given carbon; (2) the total carbon atoms in all W substituents is 15 or fewer, preferably 10 or fewer, more preferably 6 or fewer; and (3) two W's together can form a ring when taken together with the remainder of the atoms to which they are attached (e.g., as in a psoralen);
 Y and Z independently represent H, F or lower alkyl (usually 5 of fewer carbons, preferably 3 or fewer); and
 each R$_1$, independently represent H, or a hydroxy-protecting or hydroxy-coupling group capable of protecting or coupling a hydroxy group during synthesis of a polynucleotide or one or two (preferably two) R$_1$ represent a phosphate, a nucleotide or a polynucleotide connected to the compound.

The oxygen atom or other non-C atom (if present) of a functional group (such as an ether or carboxylate) that bridges the B—X linkage often arises from a hydroxyl group in the precursor of B, but is considered part of the X linker (for ease of defining the various groups) in this and the following formulas, unless the contrary is clear from the context of the discussion.

Variations of the above formula are further described in Ser. No. 08/401,630, incorporated herein by reference.

Methods and compositions are provided for detecting a nucleic acid sequence employing at least one probe comprising a photoactive coumarin crosslinking agent as described herein. The method employs adding the crosslinkable probe to the target nucleic acid under conditions of base pairing and activating the crosslinking system, so that a covalent bond is formed between the target and the probe via the crosslinking agent.

The method is performed by combining the target nucleic acid with the crosslinkable probe in an appropriate medium for base pairing to produce an assay medium. Various types of crosslinkable probes, as described in the examples below can also be added. The nucleic acid may be DNA or RNA, single or double stranded, or other molecule which comprises pyrimidines and/or purines or their analogs capable of base pairing. After sufficient time for the probe(s) to bind to the target nucleic acid the crosslinking system is activated resulting in covalent bonding between the probe(s) and the target.

In describing the subject invention, the probe will be considered first. The desired probe will have a sequence of at least about 10, more usually at least about 15, preferably at least about 16 or 17 and usually not more than about 1 kilobases (kb), more usually not more than about 0.5 kb, preferably in the range of about 18 to 200 nucleotides (nt), and frequently not more than 60 nucleotides, where the sequence is homologous to the target sequence. Homologous as used herein refers to complementary sequences. For example, for the most part, adenosine pairs with thymidine (or uridine), and guanosine pairs with cytidine. Generally, the total number of nucleotides which are homologous to the target sequence will be at least about 10 nt, more usually at least about 15, preferably at least about 16, 17 or at least 25 nt, and usually not more than about 1 or 1.2 kb, usually not more than about 0.5 kb, preferably in the range of about 18 to 200 nt.

There are extensive methodologies for providing crosslinking upon hybridization between the probe and the target to form a covalent bond. Conditions for activation may include photonic, thermal and chemical, although photonic is the primary method, but may be-used in combination with the other methods of activation. Therefore, photonic activation will be primarily discussed as the method of choice, but for completeness, alternative methods will be briefly mentioned.

The probe complementary sequence which binds to the target will usually be naturally occurring nucleotides, but in some instances the phosphate-sugar chain may be modified, by using unnatural sugars, by substituting oxygens of the phosphate with sulphur, carbon, nitrogen, or the like, by modification of the bases, or absence of a base, or other modification which can provide for synthetic advantages, stability under the conditions of the assay, resistance to enzymatic degradation, etc.

In addition, the probe may terminate with a label (including ligand) which allows for detection, such as a radiolabel, fluorophore, chemilumiphore, fluorogenic substrate, chemilumigenic substrate, biotin, antigen, enzyme, photocatalyst, redox catalyst, electroactive moiety, a member of a specific binding pair, or the like, for detection of the crosslinked probe.

In carrying out the assay, the sample may be subjected to prior treatment. The sample may be a cellular lysate, isolated episomal element, e.g., YAC, plasmid, etc., virus, purified chromosomal fragments, cDNA generated by reverse transcriptase, amplification product, mRNA, etc. Depending upon the source, the nucleic acid may be freed of cellular debris, proteins, DNA, if RNA is of interest, RNA, if DNA is of interest, size selected, gel electrophoresed, restriction enzyme digested, sheared, fragmented by alkaline hydrolysis, or the like.

The probe and target will be brought together in an appropriate medium and under conditions which provide for the desired stringency to provide an assay medium. Therefore, usually buffered solutions will be employed, employing salts, such as citrate, sodium chloride, tris, EDTA, EGTA, magnesium chloride, etc. See, for example, *Molecular Cloning: A Laboratory Manual*, eds. Sambrook et al., Cold Spring Harbor Laboratory, Cold Spring Harbor, N.Y., 1988, for a list of various buffers and conditions, which is not an exhaustive list. Solvents may be water, formamide, DMF, DMSO, HMP, alkanols, and the like, individually or in combination, usually aqueous solvents. Temperatures may range from ambient to elevated temperatures, usually not exceeding about 100° C., more usually not exceeding about 90° C. Usually, the temperature for photochemical and chemical crosslinking will be in the range of about 20 to 60° C. For thermal crosslinking, the temperature will usually be in the range of about 70 to 120° C.

The ratio of probe to target nucleic acid in the assay medium may vary, or be varied widely, depending upon the amount of target in the sample, the nature of the crosslinking agent, the detection methodology, the length of the homology between the probes and the target, the differences in the nucleotides between the target and the probe, the proportion of the target nucleic acid to total nucleic acid, the desired amount of signal amplification, or the like. The probes may be about at least equimolar to the target but are usually in substantial excess. Generally, the probe will be in at least 10 fold excess, and may be in $10^6$ fold excess, usually not more than about $10^{12}$ fold excess, more usually not more than about $10^9$ fold excess in relation to the target.

Where the target nucleic acid in the sample is double stranded, it will usually be denatured, where denaturation can be achieved chemically or thermally. Chemical denaturation may employ sodium hydroxide in an appropriate buffered medium, e.g., tris-EDTA (TE).

The amount of target nucleic acid in the assay medium will generally range from about 0.1 yuctomol to about 100 pmol, more usually 1 yuctomol to 10 pmol. The concentration of sample nucleic acid will vary widely depending on the nature of the sample. Concentrations of sample nucleic acid may vary from about 0.01 $\mu$M to 1 $\mu$M.

Where chemical denaturation has occurred, normally the medium will be neutralized to allow for hybridization. Various media can be employed for neutralization, particularly using mild acids and buffers, such as acetic acid, citric acid, etc. The particular neutralization buffer employed is selected to provide the desired stringency for the base pairing during the subsequent incubation.

Conveniently the stringency will employ about 1×–10× SSC or its equivalent. The solution may also contain a small amount of an innocuous protein, e.g. serum albumin, β-globulin, etc., generally added to provide a concentration in the range of about 0.5 to 2.5%. The base pairing may occur at elevated temperature, generally ranging from about 20 to 65° C., more usually from about 25 to 60° C. The incubation time may be varied widely, depending upon the nature of the sample, generally being at least about 5 minutes and not more than 6 hours, more usually at least about 10 minutes and not more than 2 hours.

After sufficient time for the base pairing to occur, the crosslinking agent may be activated to provide crosslinking. The activation may involve light, heat, chemical reagent, or the like, and will occur through actuation of an activator, e.g. a means for introducing a chemical agent into the medium, a means for modulating the temperature of the medium, a means for irradiating the medium and the like. Where the activatable group is a photoactivatable group, the activator will be an irradiation means where the particular wavelength which is employed may vary from about 250 to 650 nm, more usually from about 300 to 450 nm. The intensity will depend upon the particular reaction and may vary in the range of about 0.5 W to 250 W. Activation may then be initiated immediately, or after a short incubation period, usually less than 1 hour, more usually less than 0.5 hour. With photoactivation, usually extended periods of time will be involved with the activation, where incubation is also concurrent. The photoactivation time will usually be at least about 1 minute and not more than about 2 hours, more usually at least about 5 minutes and not more than about 1 hour.

The resulting compositions will comprise a probe(s) crosslinked to a target sequence. Thus, the probes comprising the crosslinking system described herein may be used to identify complementary sequences, to isolate target sequences having complementary sequences, and the like. The compositions find particular use in identifying the presence of the target sequence in the sample.

Conveniently, gel electrophoresis may be employed and the amount of cross-linked probe to target determined by the presence of a radioactive label on the probe using autoradiography; by staining the nucleic acid and detecting the amount of dye which binds to the crosslinked probe; by employing an antibody specific for the crosslinked nucleic acid duplex, particularly the cross-linked area, so that an immunoassay may be employed; or the like.

Instead of separating the hybridized nucleic acid (probe/target) from the assay medium, detection techniques can be employed which allow for detection during the course of the assay. To provide a more quantitative measurement, one can use controls having a known amount of target sequence and compare the signals observed with the sample and control.

A number of different labels that can be used with the crosslinkable probe(s) are known in the art. For example, by having a label which is a member of a specific binding pair, e.g., antibody and ligand, such as digoxigenin and anti-digoxigenin, biotin and streptavidin, sugars and lectins, etc., one has the opportunity to separate the crosslinked nucleic acid on a solid support, e.g., container surface or bead, e.g., magnetic bead. By having a label that may provide a detectable signal, either indirect or direct, where the detectable label becomes crosslinked to the target nucleic acid one has the opportunity to detect when said crosslinked nucleic acid has been separated onto a solid support or in some manner isolated. Labels may include fluorophores, chemiluminescers, radiolabels, and the like. For indirect detection, one will usually have a ligand which binds to a reciprocal member, which in turn is labeled with a detectable label. The detectable label may be any of the above labels, as well as an enzyme, where by adding substrate, one can determine the presence of crosslinked probe.

Due to the covalent crosslink, stringent washes can be used to remove background. "Stringent" conditions are readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to anneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press (1989), and include the use of washing solution and hybridization conditions (e.g., temperature, ionic strength and %SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

In a preferred embodiment herein, the wash conditions are 1×SSC, 0.1% Tween-20. In another preferred embodiment the wash conditions are 0.1% SDS, 0.01×SSC and 0.001% Tween-20.

A diverse range of target sequences can be determined in accordance with the subject protocols. The subject methodology may be used for the detection and typing of bacteria and viruses, plasmid encoded antibiotic resistance genes, and for humans, plants and animals assaying for genetic mutations, genetic diseases, genotyping for trait analysis and genotyping of polymorphic sequences. As such the methodology may be used for the detection of veterinary infections in commercial livestock, fish stocks and pets, the sexing of animals, the analysis of water systems for contamination by microorganisms, and the like.

Among bacterial and viral diseases are: *Chlamydia trachomatis, Neisseria gonorrhoeae, Mycobacteria tuberculosis, Haemeophilus ducreyi* (chancre, chancroid), *Treponema pallidium* (syphilis), *Helicobacter pylori, Mycoplasma, Pneumocystic carinii, Borrelia burgdorferi* (Lyme disease), Salmonella, Legionella, Listeria monocytogenes, HIV I and II, HTLV-II, Hepatitis A, B, C, and D, Cytomegalovirus, human Papillomavirus, Respiratory syncytial virus, Epstein-Barr virus, Dengue (RNA virus), Eastern and Western Encephalitis virus (RNA viruses), Ebola virus, and Lassa virus.

*Chlamydia trachomatis* is the cause of the most prevalent sexually transmitted disease in the U.S., leasing to 4 million cases annually. Nucleic acid targets useful for detecting all 15 serovars of *C. trachomatis* include: 16S ribosomal RNA gene and the rRNA itself, and the major outer membrane protein (MOMP) gene. *C. trachomatis* also contains a highly conserved 7.5 kb cryptic plasmid. All serovars contain this plasmid and there are typically 7–10 copies of the plasmid per elementary body.

*Neisseria gonorrhoeae*, the cause of gonorrhoeae, has species specific sequences useful for its detection, which include: 16S ribosomal RNA gene and the rRNA itself; a 4.2 kb cryptic plasmid that is present in 96% of all clinical isolates with approximately 30 copies present in each bacaterium; and the cppB gene, typically present on the plasmid, is present in all strains, including those lacking the plasmid.

*Mycobacterium tuberculosis*, the cause of tuberculosis, has species specific nucleic acid sequences useful for detection, which include: 16S ribosomal RNA gene and the rRNA itself; and an insertion sequence, IS6110, specific for the *M. tuberculosis* complex, which comprises *M. tuberculosis, M. africanum* and *M. microti*. The copy number of the insertion sequence varies from 1–5 copies in *M. bovis* to 10–20 copies in *M. tuberculosis*.

Salmonella has species specific genes which include: an insertion sequence IS200; invAgene, himA gene; and the Salmonella origin of replication, ori. The invA gene has been identified in 99.4% of about 500 strains of Salmonela tested. This gene codes for proteins essential for invasion by the Salmonella organism into epithelial cells. In addition, 142 strains from 21 genera of bacteria different from Salmonella were all found to lack the invA gene. Similarly, the insertion sequence IS200 has been identified in almost all Salmonella strains. One additional advantage in targeting the IS200 sequence is the presence of multiple gene copies in most strains of Salmonella.

Hepatitis B virus is a DNA virus with an unusual genomic organization. Virions are likely to be detected in the blood. There is a high degree of conservation in many regions of the genome. The genome is small, 3.2 kb, and, with overlapping reading frames, there is strong selection pressure against sequence variation. Candidate probes from the overlap between the polymerase and S antigen coding regions include:

GTTTTTCTTGTTGAACAAAAATCCT (SEQ ID NO:1) and

TTTCTAGGGGGAACACCCGTGTGTCT (SEQ ID NO:2), where the probe would include at least about 12 nt coming within the indicated sequences.

Hepatitis delta is a single-stranded RNA genome that is encapsulated in Hepatitis B virus coat proteins. Delta infection requires simultaneous or preexisting HBV infection and generally aggravates the clinical condition. Virions containing either the delta or HBV genome may be detected in blood samples. The delta genome encodes one known protein, the delta antigen, that is believed to be required for replicating the viral RNA genome (cellular constituents are also required). Sequences of interest as probes come within the sequence:

CTGGGAAACATCAAAGGAATTCTCG-GAAAGAAAGCCAGCAGTCTCCTCTTTACAGA AAAG (SEQ ID NO:3).

Cytomegalovirus has a large linear double-stranded DNA genome. The virus is found in blood and to a limited extent infects lymphocytes and is also found in urine. There are repeated regions in the genome allowing for detection of such repeated regions. Where only limited viral transcription has occurred, the Immediate Early Region would be the target, while for productive infection, probes to the viral glycoprotein genes would be employed.

Human papillomavirus is a circular double-stranded DNA and probes may be targeted to any region of the genome. Of particular interest are probes to the E6/E7 coding region, where one may discriminate between genotypes, e.g., HPV 16 and 18, of interest in North America, while other genotypes, such as 31, 33, 35, 51, and 53 may be diagnostic for cervical cancer in other parts of the world.

Epstein-Barr virus, the causative agent of mononucleosis and lymphocytic cancers, may be assayed in the sputum.

For acute viral infections, such as Ebola and Lassa, a rapid test not dependent on antibody formation could be of advantage in treating the patient. CSF fluids may be monitored for bacterial and viral infections, resulting in meningitis and encephalitis. Transplant patients may be monitored for CMV, herpes, BK and JC viruses.

In the case of plasmid-encoded antibiotic resistance genes, there is great concern whether a pathogenic organism is resistant to one or more antibiotics. Vancomycin is an extremely important drug for treatment of strains of Staphylococcus and Streptococcus that are resistant to other antibiotics. Some strains of enterococcus are resistant to vancomycin. Probing for vancomycin resistance may serve to reduce the transmission of vancomycin resistance. Probes for detecting vancomycin resistance include:

CATAGGGGATACCAGACAATTCAAAC (SEQ ID NO:4);

ACCTGACCGTGCGCCCTTCACAAAG (SEQ ID NO:5);

ACGATGCCGCCATCCTCCTGCAAAA (SEQ ID NO:6); and

CACAGACCATTCGCAGTATTGAAAAC (SEQ ID NO:7).

Other targets of interest are the TEM-1 gene (β-lactamase) found in Enterobacteriaceae; TEM-1 gene in penicillinase producing *N. gonorrhoeae* (PPNG) plasmid; genes conferring aminoglycoside antibiotic resistance; genes conferring erythromycin resistance; and genes conferring rifampin resistance, especially associated with *M. tuberculosis*.

Among human genetic targets, genes encoding factor II, factor V, and hemochromatosis display genetic variations which are known to cause diseases.

Prothrombin (factor II) is the precursor of thrombin, which is a controlling factor in hemostatis and thrombosis. A genetic variation in the 3' untranslated region of the prothrombin gene, (20210 G->A) is thought to negatively effect the regulation of gene expression and is associated with increased risk for deep vein thrombosis. The genetic variation in the prothrombin gene is also associated with significantly increased risk for myocardial infarction when other risk factors are present, such as smoking or obesity.

The factor V Leiden mutation (1691 G-A) is the cause of 90% of the cases of individuals who display resistance to Activated Protein C, which is the most common cause of inherited thrombophilia. This genetic mutation leads to the synthesis of factor V a protein with decreased rates of inactivation by APC.

Genetic hemochromatosis is an autosomal recessive disorder that causes an iron overload. Two mutations in the common hereditary hemochromatosis gene, C282Y and H63D, have been linked to significantly higher risk for an individual to develop hemochromatosis. The disease is characterized by high cellular iron levels causes tissue damage, in particular in the liver, pancreas, joints, heart and pituitary gland. Incidence of this disease is estimated to be 1 in 300 in northern European populations.

Also of interest is amniocentesis or other procedure for isolating fetal DNA, where the interest may be in the sex of the fetus, gross chromosomal aberrations, e.g., Down's syndrome, where one would quantitate the level of chromosome 21.

Other genetic targets of interest are sequence variations referred to as single nucleotide polymorphisms (SNPs). Generally, the previous examples involve a single nucleotide change in a single gene that is severe enough to cause disease in the patient (monogenic disease). However, many other genetic sequence variations are present which do not directly cause disease. These polymorphisms however may act in concert with one or several other genotypes or environmental factors to produce a disease phenotype. The first of this type of polymorphism to be studied was the ABO blood group polymorphism, whose antigenic variation is due to severly single nucleotide polymorphisms. Nevertheless, the subject methodology can be used for the detection of such single nucleotide polymorphisms in the same manner as for the mutation assays.

Kits are provided comprising at least one probe capable of cross-linking as described previously. The probes are labeled to allow for easy detection of cross-linked nucleic acids. One may use radioactive labels, fluorescent labels, specific binding pair member labels, and the like. The probes include sequences for hybridizing to a target nucleic acid.

The Center for Disease Control recommends that positive results from non-culture diagnostic assays be confirmed by ancillary testing.

The confirmation assay herein provides for using two capture probes with the same sequence where one probe is labeled with, e.g., a specific member binding pair, and the other probe does not contain that label. Thus, these two types of probes will "compete" to hybridize with target sequence that may be present in the assay medium.

To the extent that the non-labeled probe binds to the target sequence, the signal in the assay will be proportionately reduced. For example, if the ratio of non-labeled probe to labeled probe is 9:1, then the signal in this assay will be reduced by ~90% compared to the signal obtained in an assay of the same sample using only the labeled probe.

The following examples are offered by way of illustration and not by way of limitation.

EXAMPLE 1

Preparation of Photoactivatable Compound in Capture Probes

Preparation of the Photocrosslinker Reagent 1-O-(4,4'-Dimethoxytrityl)-3-O-(7-coumarinyl)-2-O-(β-cyanoethyl-N,N-diisopropylphosphoramidite)glycerol The title compound, prepared in four steps starting from 7-hydroxycoumarin, is useful for incorporating the photocrosslinker into any position in the sequence of an oligonucleotide via automated synthesis.

Synthesis of 7-glycidyl coumarin: To 270 mL acetone in a reaction flask equipped with a reflux condenser was added 7-hydroxycoumarin (16.2 g), epibromohydrin (15.8 g) and potassium carbonate (13.8 g) and the mixture was refluxed for 18 h. After cooling the reaction mixture, 100 mL 5% sodium hydroxide (aqueous) was added and the solution was extracted three times with 80 mL methylene chloride. The extracts were combined and the solvent removed by rotary evaporation to give the crude product as a yellow solid (1.5 g). The product was purified by recrystallization from hexane:acetone (3:2) at 4° C. to afford a white powder (290 mg): mp 110–112° C.; TLC (8% v/v ethyl acetate/chloroform) $R_f$=0.6.

Synthesis of 1-O-(7-coumarinyl)glycerol: 7-Glycidyl coumarin (2.0 g) was dissolved in 80 mL acetone and 50 mL 1.8 M sulfuric acid, and the solution was refluxed for 20 minutes. The solution was cooled to room temperature, neutralized with 1.6 M ammonium hydroxide, and extracted three times with 50 mL ethyl acetate. The combined extracts were evaporated to yield the product as a white solid (1.40 g): mp 118–120° C.

Synthesis of 1-O-(4,4'-Dimethoxytrityl)-3-O-(7-coumarinyl)glycerol: The starting material 1-O-(7-coumarinyl)glycerol (1.37 g) was dried by coevaporation with 11 mL pyridine, repeated three times. To the dried material was added 45 mL pyridine, 0.33 mL triethylamine, 4-dimethylaminopyridine (44 mg) and dimethoxytrityl chloride (1.78 g). The solution was stirred at room temperature for 3 h, 66 mL water was added, and the solution was extracted three times with 35 mL methylene chloride. The organic extract was dried with sodium sulfate and the solvent was removed to give the crude product. Purification by silica gel column chromatography using hexane:acetone:triethylamine (70:28:2) yielded the product as a white solid (2.6 g): TLC (same solvent) $R_f$=0.43.

Synthesis of 1-O-(4,4'-Dimethoxytrityl)-3-O-(7-coumarinyl)-2-O-(β-cyanoethyl-N,N-diisopropyl phosphoramidite)glycerol: The starting material 1-O-(4,4'-Dimethoxytrityl)-3-O-(7-coumarinyl)glycerol was dried by coevaporation with 12 mL pyridine:chloroform (3:1), repeated twice. The resulting viscous liquid was dissolved in 10 mL pyridine:chloroform (1:1) and added under argon with rapid stirring to a flask containing 10 mL methylene chloride, 3 mL N,N-diisopropylethylamine, and β-cyanoethyl-N,N-diisopropyl chlorophosphoramidite (1.8 g). The solution was stirred for 90 minutes. The solution was diluted with 60 mL ethyl acetate and 3 mL triethylamine, then washed twice with 50 mL saturated aqueous sodium chloride. The organic phase was dried with sodium sulfate and the solvent was removed to give the crude product. Purification by silica gel column chromatography using hexane:acetone:triethylamine (70:28:2) yielded the product as a viscous, clear oil (2.6 g): TLC (hexane:acetone, 4:1) $R_f$=0.20.

Oligonucleotide synthesis: For use in automated oligonucleotide synthesis, the photocrosslinking reagent was dissolved in dry acetonitrile at a concentration of 0.5 g/mL. The bottle of the solution was affixed to an extra port on the synthesizer and incorporated via the preprogrammed protocol. After automated synthesis, the oligonucleotide was cleaved from the solid support and deprotected with 3 mL 30% ammonium hydroxide for 2 h at room temperature. The ammonium hydroxide was removed in vacuo, and the oligonucleotide was purified to homogeneity by denaturing polyacrylamide gel electrophoresis. Stock solutions in distilled, de-ionized water were prepared and stored until use at −20° C.

EXAMPLE 2

Assay for Human Papilloma Virus Type 16 Using a Probe Comprising a Non-Nucleosidic Coumarin Using the reagent prepared in Example 1, oligonucleotides were prepared via the β-cyanoethylphosphoramidite method of DNA synthesis that were identical to segments of the genome of human papilloma virus type 16. The oligonucleotides were complementary to nucleotides 89–108 and 283–302 of the E6 gene, respectively (the sequence of which is herein incorporated by reference). In each molecule, the 5' terminal nucleotide of the natural sequence (adenosine) was replaced by 3-(7-coumarinylmethyl) glycerol. The 3' end terminated with a biotin moiety.

In parallel, two additional DNA molecules were synthesized. These oligonucleotides had complementary sequences to either nucleotides 89–108 or 283–302 of the E6 gene; however, in these modified oligonucleotides 3-(7-coumarinylmethyl) glycol was replaced by the nucleosidic coumarin derivative described in Saba et al., U.S. Pat. No. 5,082,934, by using the 3'-O-(N,N-diisopropylphosphoramidite) 5'-O-(4,4'-dimethoxytrityl) derivative at the 5' position of the 2'-deoxyribonucleotide, herein referred to as the "Saba compound."

After assembly, the four oligonucleotides were cleaved from the solid support with 1 ml 30% NH$_4$OH for 1.5 hours at room temperature. The ammonia solution was then heated at 55° C. for a further 1.5 hours. After cooling, the NH$_4$OH was removed in vacuo. The crude oligonucleotides were purified to homogeneity by high performance liquid chromatography.

The oligonucleotides were hybridized in 0.75 M NaCl buffer (20 μl) with complementary 5'-$^{32}$P-labeled oligonucleotides (molar ratio of unlabelled:labelled oligonucleotides=100:1) for 1 hour at 40° C. At this time the solutions were irradiated with UV-B wavelength light (XL 1500 UV crosslinker, Spectronics, Inc.) for 15 minutes. The extent of crosslinking (with respect to the radiolabeled targets) was determined by denaturing polyacrylamide gel electrophoresis followed by scintillation counting of the excised bands. The results are set forth in the following table:

| E6 Gene Sequence Position | Crosslinker Used in Oligonucleotide | Crosslinking Reaction Site 5'–3' | Crosslinking Efficiency % |
|---|---|---|---|
| 89-108 | 3-(7-Coumarinylmethyl) glycerol | TTT | 64% |
| 89-108 | Saba compound | TTT | 54% |
| 283-302 | 3-(7-Coumarinylmethyl) glycerol | TTT | 76% |
| 283-302 | Saba Compound | TTT | 68% |

The results indicate that the compounds of the current invention undergo photochemical crosslinking more efficiently than the compound of U.S. Pat. No. 5,082,934 (>10% greater relative efficiency).

EXAMPLE 3

Assay for Factor V Leiden Mutation

The photo-crosslinking technology described herein was employed in the development of a direct assay for factor V Leiden, a point mutation in the factor V gene (G 1691A) that is the most common inherited risk factor for thrombosis. This crosslinking hybridization assay utilized two allele-specific capture probes and six signal generating reporter probes; all were modified with a photo-activated crosslinking compound. By utilizing two different capture probes complementary to a 16-base sequence at the factor V Leiden mutation site, but differing in the nucleotide opposite the mutation site (C versus T), wild-type and factor V Leiden alleles were differentiated in purified DNA specimens. The assay was also successfully applied to genomic DNA in leukocytes isolated from whole blood; the factor V status of 122 patients as determined by this method was in complete concordance with a standard PCR-based assay and clearly discriminated between normal individuals and factor V Leiden heterozygotes.

Current methods of detection for factor V Leiden are labor-intensive, requiring purification of genomic DNA from peripheral blood leukocytes, amplification by PCR of the region of the factor V gene flanking the factor V Leiden mutation site and analysis of the amplification products by gel electrophoresis coupled with either restriction enzyme digestion or hybridization with allele-specific oligonucleotide probes (Dahlback B. (1995), *Thromb Haemost* 73:739–42). In addition, current "home brew" methods are time-consuming and expensive, suffer from a lack of standardization and require a level of expertise and equipment not routinely available outside academic medical centers. Since factor V Leiden is the most common cause of inherited thrombophilia yet identified, a simple test to determine the factor V genotype would be a valuable asset in identifying those individuals predisposed to the condition. The results below show that herein is a simple and standardized test for factor V Leiden, in particular, a direct detection assay for the presence of the factor V Leiden point mutation is provided which is sensitive and convenient. The assay utilizes the novel nucleic acid crosslinking technology provided herein and requires no prior purification or amplification of the genomic DNA.

Materials and Methods

Patient Samples

Patient samples were obtained from individuals referred to the Stanford Laboratory for factor V Leiden determination, the majority of whom had a history of venous thrombosis. Previously we reported that this unselected group of individuals had a 20% prevalence of factor V Leiden, consistent with reports from other institutions testing similar patient groups (Svensson P. J., et al. (1994), *N Engl J Med* 330:517–22; Dahlback B. (1995), *Thromb Haemost* 73:739–42) Peripheral blood was collected in EDTA tubes and either assayed the same day or after storage for 3 days at 4° C. Alternatively, leukocytes were isolated from fresh blood and stored or −70° C. for three days prior to testing.

Oligonucleotide Synthesis

Oligonucleotides complementary to sequences within exon 10 and intron 10 of the factor V gene were synthesized on a PerSeptive Expedite 8909 Synthesizer using Expedite DNA synthesis reagents (PerSeptive Biosystems, Framingham, Mass.). Two types of oligomer were synthesized:

(i) Allele-specific capture probes complementary to nucleotides 1683–1698 of either the normal factor V gene or the mutant factor V (Leiden) gene. These probes contained a biotin molecule at the 3' terminus (BioTEG CPG; Glen Research, Stirling, Va.) and a photo-active coumarin crosslinking agent that was positioned opposite the thymidine residue at position 1697 of the exon 10 sequence (in place of the normal dA residue). To enable incorporation of the crosslinker into the oligonucleotides during automated synthesis, a filly protected phosphoramidite derived from 7-hydroxy coumarin, 1-O-(4,4'-dimethoxytrityl)-3-O-(7-coumarinyl)-2-O-(2-cyanoethyl-N,N-diisopropylphosphoramidite)glycerol, was prepared (described above).

(ii) Crosslinker-modified reporter probes complementary to non-allele specific regions of exon 10 and intron 10 of the factor V gene. These probes were fluoresceinated at the 5' terminus during synthesis (Fluorescein CE Phosphoramidite; Cruachem Inc., Dulles, Va.). Six reporter probes were synthesized; these were complementary to nucleotides 1448–1468, 1514–1537, 1558–1580 and 1699–1623 of exon 10 and to nucleotides 61–82 and 89–111 of intron 10.

Post synthesis, the probes were cleaved from the solid support and deprotected by incubating the support in concentrated ammonium hydroxide for 30 min. at 55° C. The fully deprotected probes were purified via electrophoresis through denaturing polyacrylamide gels, followed by excision of the product bands and elution of the products (Zehnder J. L., et al. (1996), *Am J Clin Path* 106:107–111). The purified oligonucleotides were desalted by Sep-Pak C18 treatment using the procedure recommended by the manufacturer (Waters Corp., Milford, Mass.).

Crosslinking Hybridization Assay Procedure

Sample preparation. Red blood cells were lysed by the sequential addition of one volume erythrocyte lysis buffer (320 mmol/L saccharose, 5 mmol/L MgC12, 10 mmol/L Tris-HCl [pH 7.5], 1% Triton X-100) and three volumes water to one volume (0.5–4 mL) whole blood. Following a 10 min. incubation on ice, the samples were centrifuged at 1500 g. The supernatant was decanted and the leukocyte pellet resuspended in 750 mL 1×sodium saline citrate (SSC) buffer (150 mmol/L NaCl, 15 mmol/L sodium citrate [pH 7.0]). The cell suspension was transferred to a 2 mL microcentrifuge tube and centrifuged for 2 min. at 12,000 g. The supernatant was discarded, 330 mL leukocyte lysis reagent (280 mmol/L NaOH) added and the cell pellet resuspended by vortexing. The sample was heated in a boiling water bath for 5 min., vortexed to fully dissolve the cell debris, and then heated at 100° C. for an additional 30 min. The solution was cooled and either used directly or stored at −70° C. until required.

Assay setup and procedure. Determination of the factor V genotype by this assay is based ultimately on the comparison of the fluorescent signals obtained from each sample after hybridization and crosslinking of the sample DNA to different sets of allele-specific probes. Overviews of the assay format and procedure are shown in FIGS. 1 and 2. Each processed sample was aliquoted (100 mL) into three wells of a 96 well polypropylene microtiter plate (Corning Costar Corp., Cambridge, Mass.). One of three different probe solutions (50 mL, containing 1.5 mol/L NaCl, 35% formamide, 0.5% bovine (serum albumin) was added to each aliquot. The first probe solution contained six crosslinker-modified reporter probes (0.1 pmole each) complementary to a region of the factor V gene flanking the mutation site and a single crosslinker-modified capture probe (1 pmole) that was complementary to nucleotides 1683–1698 of the normal factor V gene: 5'-TXT TCC TCG CCT GTC C-3' (SEQ ID NO:8) (X denotes the position of the crosslinker in the probe).

The second probe solution contained the same set of reporter probes as the first, however the included capture probe was complementary to the mutant factor V (Leiden) gene sequence: 5'-TXT TCC TTG CCT GTC C-3' (SEQ ID NO:9).

A third, control, probe solution contained the reporter probe set and both the normal- and mutant-specific capture probes.

In addition to the samples, each assay plate also contained nine negative controls (unboiled leukocyte lysis reagent) and three positive controls. Each of the three probe reagents was added to three negative control wells and one positive control well. Positive control wells contained an exon 10—partial intron 10 PCR amplicon (50 amoles) dissolved in leukocyte lysis reagent. The target DNA had been obtained previously by PCR amplification of DNA from a patient heterozygous for the factor V Leiden allele (see below for PCR procedure). Following addition of the probe reagents to the samples and controls, 50 μL neutralization reagent (190 mmol/L citric acid, 300 mmol/L NaH2PO4, 1.5 mol/L NaCl, 0.4% Tween-20, 35% formamide) was added to each well. The loaded microplate was covered by a 2 mm thick Pyrex™ filter and heated to 40° C. by placing it on a microplate heater (USA/Scientific, Ocala, Fla.) that was positioned inside a UV crosslinking chamber 2.5 cm below the UV lamps (UV-A bulbs, UVP Model CL1000-L; UVP, Inc., Upland, Calif.). The samples were incubated for 20 min. and then irradiated for 30 min. at the same temperature. The total energy delivered to the plate was approximately 30 mJ/cm2. Following irradiation, the plate was removed from the heater and cooled to room temperature for 10 min. Next, 75 mg streptavidin-coated magnetic beads (Dynabeads® M-280, Dynal Inc., Lake Success, N.Y.) were added to each well to capture the crosslinked probe-target hybrids via the biotin residue attached to the allele-specific capture probes. Following a 30 min. incubation at room temperature the plate was placed on top of a set of bar magnets that were positioned between the wells under the plate such that the magnetic beads in each well formed a tight pellet towards one side of the U-shaped well bottom.

After 30 seconds the liquid in each well was removed by aspiration and the plate taken off the magnet assembly. The beads were washed once by the addition of 225 mL wash reagent (1×SSC, 0.1% Tween-20) to each well. The plate was again placed onto the magnet assembly and the wash reagent removed. The plate was then removed from the magnet. Immediately after washing the beads, 100 mL anti-fluorescein antibody-alkaline phosphatase conjugate (Boehringer Mannheim Corp., Indianapolis, Ind.), diluted 1:3000 in 100 mmol/L Tris-HCl (pH 7.5), 150 mmol/L NaCl, 0.1% Tween-20, 0.25% bovine serum albumin, was added to each well. The samples were incubated for 20 min. at room temp. and then washed four times with 225 mL wash reagent using the procedure described above.

Upon completion of the final wash cycle, 100 mL of an alkaline phosphatase substrate (Attophos™; JBL Scientific, San Luis Obispo, Calif.), was added to each well and the plate incubated at 37° C. for 60 min. Finally, the fluorescent product produced from the reaction of Attophos™ with alkaline phosphatase was detected by recording the fluorescence signal with a microplate fluorometer (Packard Instrument Co., Meriden, Conn.).

Data Analysis

The net sample signal (NSS) was calculated by subtracting the mean signal of the three negative controls for each probe set (factor V normal, factor V Leiden or both) from the signal obtained from a sample tested with the appropriate probe set. Negative values for the NSS were considered to be zero. Patient genotype determinations were based on the ratio of the NSS for the mutant (Leiden) probe set divided by the NSS for the normal probe set.

Assay Precision

Within-run and between-run precision was assessed by testing a sample obtained from peripheral blood from a single individual. For within-run precision, the sample was divided into six aliquots and the assay performed six times on the same plate. For between-run precision the sample was divided into six aliquots and one aliquot was tested each day for six consecutive days.

PCR Amplicication and Genotype Determination by MNLI Digestion

Genomic DNA was obtained from whole blood by lysing red blood cells and purifying the DNA using an affinity spin-column (QIAamp, Qiagen Inc., Chatsworth, Calif.). Purified genomic DNA (50 ng) samples were amplified in 100-mL reactions containing 10 mmol/L Tris-HCl (pH 8.3 at 25° C.), 50 mmol/L KCl, 1.5 mmol/L MgCl2; 100 mmol/L each dATP, dCTP, and dGTP; 200 mmol/L dUTP; 0.2 mmol/L each primer flanking the factor V Leiden allele (position 1691) as described in Bertina et al.(1994), *Nature* 369:64–7 and 2.5 units of AmpliTaq® DNA Polymerase or AmpliTaq Gold™ DNA Polymerase (Roche Molecular Systems, Alameda, Calif.). Samples were amplified in a Perkin-Elmer GeneAmp® PCR System 2400 (Perkin-Elmer Applied Biosystems, Foster City, Calif.) using the following profile: an initial hold of 94° C. for 30–60 seconds if using AmpliTaq® DNA Polymerase or 12 min. if using AmpliTaq Gold™ DNA Polymerase; 33 cycles of 94° C. for 10 seconds and 62° C. for 30 s; and a final extension step of 68° C. for 5 min. Total run time was 1.2 h. Amplicons were subjected to digestion with Mnl I and genotype determined by fragment size after agarose gel electrophoresis as previously described (Bertina R. M., et al. (1994), supra)

Results

Overview of Crosslinking Hybridization Assay for Factor V Leiden Mutation

The format and procedure of the crosslinking assay for detection of the factor V Leiden mutation are outlined in FIGS. 1 and 2. Each sample was analyzed with three separate probe set combinations. The first test employed a probe set containing a capture probe complementary to the normal gene sequence, the second, a probe set containing a capture probe complementary to the mutant (Leiden) gene sequence and the third, a probe set containing both normal and mutant capture probes.

Assay conditions were optimized for minimal hybridization and crosslinking between probe/target combinations containing a mismatch, while permitting efficient hybridization and crosslinking between fully complementary probe/target combinations. The genomic DNA from an individual with two normal factor V alleles should yield a relatively strong signal when subjected to the normal capture probe set and a weak signal when subjected to the mutant probe set under the assay conditions. The reverse outcome should be true for individuals who are homozygous factor V Leiden, those individuals whose factor V gene contains two mutant alleles. For individuals who are heterozygous for factor V Leiden (one copy of each allele) each probe set should yield approximately the same signal. The control test, which includes both capture probes, should always deliver the same relative signal, irrespective of genotype. The predicted relative signal intensities obtained from the three factor V genotypes after testing with the normal, mutant and control probe sets should be 2, 0 and 2 for the normal genotype, 0, 2 and 2 for the factor V Leiden homozygote, and 1, 1 and 2 for the factor V Leiden heterozygote, respectively.

The absolute signal obtained from testing individuals with the same genotype will vary due to the amount of blood available for testing and variations in subject leukocyte concentration. Consequently, determination of the factor V genotype was based on the ratio of the NSS generated by the mutant (Leiden) probe set divided by the NSS generated by the normal probe set. Accordingly, the theoretical NSS ratios for a normal individual, a heterozygote and a factor V Leiden homozygote should be zero, one and infinity.

Crosslinking Hybridization Assay Performance

Assay performance with purified factor V gene fragments. Initial evaluations of assay performance were conducted with purified PCR amplicons derived from genomic DNA of a normal individual, a factor V Leiden heterozygote and a factor V Leiden homozygote (see Table 1). These results indicated that the assay, as predicted, was capable of distinguishing all three genotypes.

TABLE 1

Test Data on PCR Amplicons Derived From Normal, Factor V Leiden Heterozygous and Factor V Leiden Homozygous Individuals

| Factor V Genotype | Net Sample Signal (Relative Fluorescence Units) | | | Leiden Normal |
|---|---|---|---|---|
| | Normal Probes | Leiden Probes | Both Probes | |
| Normal | 396 | 36 | 455 | 0.09 |
| Heterozygous | 148 | 161 | 360 | 1.08 |
| Homozygous | 12 | 633 | 536 | 52.75 |

Assay performance with samples obtained from whole blood. To assess the assay, whole blood was collected from a single individual previously determined to possess a normal factor V genotype (results not shown). To test signal response to cell concentration, the blood was divided into aliquots with three different leukocyte concentrations. Additionally, to evaluate the possible effect of storage and transport conditions, assays were carried out directly on leukocytes isolated from fresh or refrigerated blood and on previously isolated leukocytes stored at −70° C. The results in FIG. 3 show that sufficient signal for genomic resolution was obtained even at the lowest cell number tested ($0.7 \times 10^7$ leukocytes/test well). Furthermore, the performance of the assay was not altered significantly as a result of the three sample processing methods tested. The data showed that, as expected, the assay signal increased with increased levels of leukocytes tested. However, unlike experiments with purified DNA targets, there was not a direct correlation between target concentration and the level of signal generated (data not shown).

Precision studies were carried out to determine the within-run and between-run reproducibility of the assay. Within-run precision was calculated after performing the assay on six identical samples (normal factor V genotype), while between-run precision was determined following testing of a single same sample each day for six days. The results of these experiments, shown in Table 2, indicated that within-run and between-run CV's were within acceptable limits. Although the data indicated slightly better between-run precision than within-run precision, it is noted that the sample size (n=6) for these studies was relatively small. It is reasonable to conclude that the within-run CV's determined here (8.3%–10.1%) are a realistic representation of the precision of this assay.

TABLE 2

Summary of Assay Precision Studies (n = 6)

| | Coefficient of Variation, % | | |
|---|---|---|---|
| Precision Assay | Normal Probes | Leiden Probes | Both Probes |
| Within-Run | 8.3 | 9.9 | 10.1 |
| Between-Run | 6.5 | 6.6 | 2.6 |

Testing of patient samples. The factor V Leiden status of 122 patients referred for evaluation for deep vein thrombosis were tested by the crosslinking hybridization assay and by the standard PCR amplification—Mnl I restriction enzyme analysis; the latter method is currently considered the gold standard for factor V Leiden mutation testing. Fourteen of these individuals were determined by the PCR amplification method to be heterozygous for the factor V allele while the remaining 108 were normal.

Between 0.5–4 mL whole blood from each individual was tested by the crosslinking hybridization assay to determine their factor V genotype. Since the leukocyte concentration in the blood samples was not determined prior to testing, the amount of genomic DNA assayed in each sample was unknown. However, assuming a normal range of leukocyte concentration in whole blood of ca. $4\times10^6$–$11\times10^6$ cells/mL, it is estimated that the amount of factor V gene target copies present in each test well was between 2–40 amoles.

Following testing of the patient samples by the crosslinking hybridization assay, the ratio of the NSS for the mutant (Leiden) probe set divided by the NSS for the normal probe set was calculated for each sample. The ratios obtained for all 122 samples are summarized in FIG. 4. The mutant/normal NSS ratios for the 108 normal individuals fell between 0–0.26 (mean=0.06; mean+four SD=0.31), whereas the fourteen heterozygous individuals fell between 0.47–1.32 (mean=0.76); clear separation was observed between the two groups of patients with no overlap. Based on these results, a mutant/normal NSS ratio of 0.35 could be used as a lower limit for indicating factor V Leiden heterozygosity (dotted line of FIG. 4). None of the patients referred during the time period of this study was homozygous for the factor V Leiden allele, however, the PCR amplicon data shown above suggested that the crosslinking hybridization method would also clearly distinguish homozygotes from heterozygotes.

The data obtained from the control probe set containing both factor V allele-specific capture probes was not used to calculate factor V genotype. However, in a commercial version of this assay the data from the control would be used to ensure that the NSS values obtained from the two individual probe sets fell within acceptable limits for any given genotype. At the completion of the 122 patient study the ratios obtained by dividing the NSS for the normal probe set by the NSS for the control probe set and by dividing the NSS for the mutant (Leiden) probe set by the NSS for the control probe set were calculated. For the 108 normal individuals the normal/control NSS ratios fell between 0.67–1.81 (mean=1.08) and the mutant/control NSS ratios fell between 0–0.34 (mean=0.06). For the 14 heterozygous individuals the normal/control NSS ratios fell between 0.47–1.15 (mean=0.75) and the mutant/control NSS ratios fell between 0.33–1.11 (mean=0.56). The data set collected here suggests that a test result would be valid if an individual determined to have a normal factor V genotype had a normal/control NSS ratio between approximately 0.7–1.8 and a mutant/control NSS ratio between approximately 0–0.3. For an individual determined to be heterozygous for factor V Leiden the normal/control and the mutant/control NSS ratios should both fall between approximately 0.3–1.2. Any test that yielded normal/control or mutant/control NSS ratios outside these limits would need to be repeated.

By covalently joining the hybridized probe and target nucleic acids the amount of target retained throughout the assay procedure is maximized, thereby ensuring the highest possible signal. Furthermore, due to the fact that covalently-linked hybrids are far more stable than conventional duplex strands, adventitiously bound signal generating probes may be more efficiently removed from the test sample with washing procedures of higher stringency, thus effectively lowering background. The results from testing 122 patient samples were in total agreement with the gold standard PCR-based method; discrimination between normal and heterozygous individuals was unambiguous.

The direct assay offers certain advantages over the PCR method. For example, the assay does not suffer from problems inherent to PCR such as sample inhibition and false results due to reaction contamination. In addition, PCR methods rely on equal amplification of both genomic strands. Preferential amplification of one strand may mask the presence of the other and lead to incorrect diagnosis of heterozygous individuals.

The 96 well microtiter plate format allows for simultaneous processing of multiple patient samples. Since twelve wells are occupied by controls, a maximum of twelve samples (36 wells) may be processed during one session (the assay has a maximum capacity of 48 usable wells due to the design of the magnet assembly). The entire assay procedure, including sample preparation, can be completed in under five hours. An instrument that automates all steps of the assay procedure, including reagent addition, crosslinking, washing and fluorescence detection, is currently under development. The instrument utilizes all 96 wells, thereby increasing the single run testing capacity to 28 samples. With automation, the only manual steps remaining are those associated with sample preparation.

EXAMPLE 4

Assay for Hepatitis B Virus DNA

The nucleic acid photo-crosslinking technology as described herein was employed to quantify Hepatitis B Virus (HBV) DNA levels in serum. Crosslinker-modified DNA probes complementary to the viral genomes of the major HBV subtypes were synthesized and used in an assay that could be completed in less than six hours. The quantification range of the assay, as determined by testing serial dilutions of Eurohep HBV reference standards, was $5\times10^5$–$3\times10^9$ molecules HBV DNA/ml serum. Within-run and between-run coefficients of variation (CV) for the assay were 4.3% and 4.0%, respectively. The assay was used to determine HBV DNA levels in 302 serum samples and the results were compared to those obtained after testing the same samples with the Chiron bDNA assay for HBV DNA. Of the samples tested, 218 were positive for HBV DNA by both assays and 72 gave results below the cutoff for both assays. Of the remaining twelve samples, ten were positive for HBV DNA by the crosslinking assay only; the two other samples were positive by the bDNA assay only. Twenty eight samples had to be retested by the bDNA assay (CV>20% between the results obtained from testing each sample in duplicate) whereas only three samples required retesting by the crosslinking assay. The correlation between the HBV DNA levels, as measured by the two tests, was very high (r=0.902; P=0.01). This assays shows that the crosslinking assay described herein is a sensitive and reproducible method to detect and quantify HBV DNA levels in sera.

Hepatitis B virus (HBV) is one of the causative agents of viral hepatitis. An estimated 350 million persons worldwide are chronic carriers of the virus, with 100 million carriers in China and approximately one million in the USA (Aach, R. A., (1988), *Ann. Intern. Med.* 109:89–90; Alter, M. J., et al. (1994), *Clin. North Am.* 23.437–455). Although the majority of individuals infected with HBV resolve the primary infection and develop lasting immunity, clinical studies have shown that 5–10% of individuals are chronically infected with the virus and about 25–40% of these individuals may deteriorate and progress to cirrhosis or liver cancer (Gitlin, N. (1997), *Clin. Chem.* 43:1500–1506).

HBV is a partially double-stranded DNA virus of the class Hepadnaviradae (Gitlin, N. (1997) supra). The virus is composed of a 42 nanometer outer shell and a 27 nanometer inner shell. A major component of the outer shell is the hepatitis B surface antigen (HBsAg). The inner shell is composed of the hepatitis B core antigen (HBcAg) and a derivative, the hepatitis B e antigen (HBeAg). The detection of serological markers such as HBsAg or HBeAg are useful for diagnosis (Gitlin, N. (1997), supra). The presence of HBsAg in serum indicates HBV infection but does not provide information on the replicative state of the virus. Although HBeAg is thought to be a good marker for active viral replication, mutants that do not produce HBeAg have been found (Carman, W. F., et al. (1989), *Lancet* 0:588–591). The presence of HBV DNA in serum of chronic carriers is a better indicator for viral replication and detection and quantification of the viral DNA has been employed to study the natural progression of the disease and to monitor the response of patients receiving anti-viral therapy (Hoofnagle, J. H. (1990), *J. Hepatol.* 11:S100–S107).

Several molecular approaches have been used to quantify serum HBV DNA levels, including commercially available assays such as those from Abbott (Genostics™ HBV-DNA Assay, Abbott Laboratories, Chicago, Ill.), Digene (Hybrid-Capture™ HBV-DNA Assay, Digene Diagnostics Inc., Silver Springs, Md.), and Chiron (Quantiplex™ HBV-DNA Assay, Chiron, Emeryville, Calif.) (Butterworth, La., et al. (1996), *J. Hepatol.* 24:686–691; Janssen, H. L. A., et al. (1993), *J. Med. Virol.* 40:307–312). Current commercial HBV DNA detection assays, however, have varying levels of sensitivity and inter-assay comparisons have shown poor agreement due to a lack of standardization (Ridker P. M., et al. (1995), *N Engl J Med* 332:912–7; Dahlback B. (1995), *Thromb Haemost* 73:739–42; Zehnder J. L., et al. (1996), *Am J Clin Path* 106:107–111; Alter, M. J., et al. (1994), *Clin. North Am.* 23:437–455).

Materials and Methods

Source of clinical samples. Clinical testing of 302 serum samples for HBV DNA with the crosslinking and bDNA assays was conducted at Quest Laboratories, Singapore (200 samples) and at the Queen Mary Hospital, University of Hong Kong, Hong Kong (102 samples). Samples were obtained from patients with chronic Hepatitis B infection.

Source of HBV reference standards. Eurohep HBV reference plasma standards 1 (genotype A, HBsAg subtype adw) and 2 (genotype D, HBsAg subtype ayw) were obtained from Dr. K. Heermann, Division of Medical Microbiology, University of Goettingen, Germany. The levels of HBV DNA in these standards, as determined by the fourth round of the Eurohep trials was $4.2 \times 10^9$ HBV genomes/ml for plasma standard 1 (95% confidence interval=$3.3$–$5.1 \times 10^9$), and $3.8 \times 10^9$ HBV genomes/ml for plasma standard 2 (95% confidence interval=$2.8$–$4.8 \times 10^9$) (15). Aliquots of the Eurohep standards were serially diluted in HBV negative serum to achieve viral titers ranging from $1 \times 10^5$–$1 \times 10^8$/ml (0.1–100 megaequivalents [Meq]/ml) serum. These diluted samples were used to determine the sensitivity of the crosslinking assay.

Procedure of the crosslinking assay. Oligonucleotides complementary to the HBV genome were synthesized for the crosslinking assay as described above. Two types of oligomer were synthesized; biotin-modified capture probes and fluorescein-modified reporter probes. Both types of probe were modified with a photo-active coumarin crosslinking agent derived from 7-hydroxy coumarin, 1-O-(4,4'-dimethoxytrityl)-3-O-(7-coumarinyl)-2-O-(2-cyanoethyl-N,N-diisopropyl phosphoramidite)glycerol. To avoid problems in quantifying DNA from different HBV subtypes, the sequences for the probes were chosen from conserved regions of the HBV genome.

Samples were prepared by the addition of 30 ml lysis reagent (proteinase K/sodium dodecyl sulfate) to 300 ml serum and incubating the solution for 30 min at 65° C. Nucleic acids in the sample were subsequently denatured by the addition of 6.3 ml alkaline denaturation reagent and boiling for 15 min. The samples were cooled for 5 min and then centrifuged at 12,000×g for 5 min. Each processed sample was aliquoted (125 ml) into two wells of a 96 well polypropylene microtiter plate. In addition to the samples, each assay plate also contained the following controls supplied with the kit; two negative controls (HBV-negative serum) and four different HBV quantification standards (negative serum containing different concentrations of cloned HBV DNA, subtype adw, ranging from 3–3000 Meq/ml). Each standard was added to two wells in the microplate. Next, HBV probes and neutralization reagent were added to each sample and control well and the HBV DNA and probes were hybridized for 20 min at 45° C. Next, the samples were irradiated with a UV-A light source for 30 min to crosslink the probe-target hybrids.

Following irradiation, streptavidin-coated magnetic beads (Dynabeads® M-280, Dynal Inc., Lake Success, N.Y.) were added to each well to capture the crosslinked probe-target hybrids via the biotin residue attached to the capture probes. After 30 min the beads in the microwells were washed twice and then incubated in the presence of an anti-fluorescein antibody-alkaline phosphatase (AP) conjugate. At the end of this step each well was washed four times. Upon completion of the final wash cycle, 100 ml Attophos™ (JBL Scientific, San Luis Obispo, Calif.), was added to each well and the plate incubated at 37° C. for 60 min. Finally, the fluorescent product produced from the reaction of Attophos™ with AP was detected by measuring the fluorescent signal with a microplate reader. The concentration of HBV DNA in the samples was calculated by comparing the mean fluorescent signal produced from each sample to a standard curve that had been constructed from the results obtained from the four positive standards. The HBV DNA quantification range of the assay was 0.5–3000 Meq/ml. Samples were retested if the coefficient of variation (CV) between the results obtained from testing each sample in duplicate was greater than 20%.

Procedure of the bDNA assay. The Chiron branched DNA (bDNA) assay was performed as described in the manufacturers product insert. Briefly, this assay involved sample preparation to release HBV DNA from viral particles in serum (each sample is tested in duplicate), overnight hybridization of HBV DNA to capture probes that were bound to the wall of the microtiter plate test well and to solution-phase target probes that bound to different sequences of the HBV genome. Next, the wells were washed and bDNA amplifier probes that bound to the hybridized target probes were added. In the final steps of the assay, AP-conjugated probes that were complementary to multiple sites on the amplifier probe were added to the sample wells. The captured HBV DNA was detected and quantified by measuring the level of chemiluminescence produced after reaction of the bound AP with a dioxetane substrate and comparison of the signal with a standard curve obtained from assaying a set of HBV standards in parallel with the samples. The HBV DNA quantification range of the bDNA assay is 0.7–5700Meq/ml. Following the manufacturer's recommendations, any sample that yielded a test result with a CV greater than 20% between the two replicates was retested.

Precision of the crosslinking and bDNA assays. Within-run and between-run precision of the crosslinking and bDNA assays was conducted by testing each assay with HBV positive serum obtained from a single individual. The within-run precision of each assay was determined after performing the crosslinking or bDNA assay on six identical aliquots of the sample at the same time. The between-run precision of the two assays was measured after dividing the test sample into six identical aliquots and testing each aliquot in six independent crosslinking or bDNA assay runs.

Statistical analysis. The t-test was used to compare the difference between the mean of the results obtained using the two different assays. Regression analysis was used to define the relationships between the results of different assays on the same samples. P values of less than 0.05 were used to indicate statistical significance.

Results

Sensitivity of the crosslinking assay. The results of testing serial dilutions of the Eurohep standards in the crosslinking assay are shown in FIG. 5. From these experiments, the detection limit of the assay was determined to be 0.5 Meq/ml. The assay detected both HBV subtypes (adw and ayw) with equal sensitivity. Subsequently, the Eurohep samples were used to derive a set of HBV assay standards that were prepared by serially diluting different amounts of cloned HBV DNA (subtype adw) in serum. By comparing the signal obtained from these standards with the signal obtained from known HBV levels in the Eurohep samples it was possible to assign each standard a HBV DNA concentration based on the signal generated by actual viral DNA and not cloned plasmid DNA. These standards were then used in the assay to calculate levels of HBV DNA in unknown serum samples.

Precision of the crosslinking and bDNA Assays. Studies were performed to determine and compare the within-run and between-run reproducibility of the crosslinking and bDNA assays. The results obtained showed that the analytical precision of both assays was very good; the within-run and between-run CV's of the crosslinking assay were 4.3% and 4.0%, respectively. The precision of the bDNA assay, which was determined to be 5.5% (within-run) and 6.3% (between-run), was in accordance with previous findings (Butterworth, L. A., et al. (1996), *J. Hepatol.* 24:686–691).

Performance of the crosslinking and bDNA assays with clinical samples. The ability of the crosslinking assay to detect and quantify HBV DNA in patient samples was assessed by testing 302 serum samples and comparing the results generated to those obtained by testing the same samples with the bDNA assay. The results of this study are summarized in Table 3.

TABLE 3

Summary of Clinical Study Results

| bDNA assay result[a] | Crosslinking assay result[a] | |
| --- | --- | --- |
|  | HBV DNA positive | HBV DNA negative |
| HBV DNA positive | 218 | 2 |
| HBV DNA negative | 10 | 72 |

[a]Positive samples contained ≧ 0.5 Meq/ml or ≧ 0.7 Meq/ml HBV DNA in the crosslinking and bDNA assays, respectively.

Of the 302 samples tested, 218 contained HBV DNA by both the crosslinking and bDNA assays; 194 of these contained HBV levels within the quantification ranges of both assays. Seventy two samples contained undetectable HBV DNA levels by both assays. Out of the remaining twelve samples, ten contained measurable levels of HBV DNA by the crosslinking assay (ranging from 1.266–3.993 Meq/ml) but not by the bDNA assay; the two other samples contained measurable levels of HBV DNA by the bDNA assay (1.140 and 1.711 Meq/ml) but not by the crosslinking assay. Twenty four specimens yielded crosslinking assay results greater than the 3000 Meq/ml upper quantification cutoff. Nineteen of these samples gave a bDNA assay result greater than 3000 Meq/ml (nine of which were above the 5700 Meq/ml upper detection limit); the remaining five yielded a bDNA result ranging from 2210–2589 Meq/ml.

During testing, 28 samples (9.3%) yielded a bDNA assay result that exceeded the recommended 20% CV cutoff (between the sample replicates) for an acceptable result and required retesting. Using the same criteria, only three samples (1.0%) required retesting by the crosslinking assay.

There was no statistical difference between the mean of the HBV DNA levels obtained in the 194 samples that contained measurable HBV DNA using both assays; the crosslinking assay yielded a mean value=685.7 Meq/ml and the bDNA assay yielded a mean value=718.6 Meq/ml. To show the correlation between the results obtained from the crosslinking and bDNA assays, the HBV DNA levels in the 194 samples that contained measurable HBV DNA in both assays were plotted as shown in FIG. 6. Analysis of the results showed that the HBV DNA levels in these samples, as measured by both assays, was significantly correlated (r=0.902; P=0.01).

EXAMPLE 5

Confirmation Assay

Two types of crosslinker-containing capture probes were prepared, one type contained a biotin label for capture of the probe onto a solid support, and the other type was a probe with the identical sequence without the biotin label. The probes, complementary to sequences of the cryptic plasmid of Chlamydia trachomatis, were prepared according to the procedures of Example 3.

Sequences:
 Capture Probes
  Probe 1: 5'XAGTTAATCCCAGACGCAXAATT(SEQ ID NO:10)
  Probe 1B: 5'XAGTTAATCCCAGACGCAXAATTB (SEQ ID NO:11)
  Probe 2: 5'XAGAAGATTTTCGTTATAGGAGGACAXAT (SEQ ID NO:12)

Probe 2B: 5'XAGAAGATTTTCGTTATAGGAGGACAXATB (SEQ ID NO:13)

Probe 3: 5'XATTTGGTTATCTACTTTATCTTATCXAT (SEQ ID NO:14)

Probe 3B: 5'XATTTGGTTATCTACTTTATCTTATCXATB (SEQ ID NO:15)

Reporter Probes

Probe 4: 5'FYYTCTACCACCAAGAGTTGCAXAT (SEQ ID NO:16)

Probe 5: 5'FYYAXAGCTCGTAATATGCAAGAGCATTGXAT (SEQ ID NO:17)

Probe 6: 5'FYYAXAATTCACTATCCGGAGCGCTTCAXAT (SEQ ID NO:18)

Probe 7: 5'FYYGXAGACTTTGCAACTCTTGGTG (SEQ ID NO:19).

X=7-coumarinyl glycerol

B=biotin

F=fluorescein

Y=glycerol (symmetric branch)

The three sets of probes were combined, using 0.25 pmol of biotinylated probe and 2.25 pmol of non-biotinylated probe, to give a ratio of biotinylated:non-biotinylated probe of 1:9. This probe mixture (probes 1=3B) and a set of reporter probes (probes 4–7) were substituted into the probe solution of Example IV, and the same procedures were used to assay for the presence of Chlamydia trachomatis.

Results

| | Signal [RFU] | |
|---|---|---|
| Type of Capture Probes | Negative Control | Sample |
| biotinylated probe | 47 | 253 |
| biotinylated/non-biotinylated (1:9) probe | 45 | 69 |

=>net signal is reduced by 88% net signal 1=253−47=206 net signal 2=69−45=24

The percentage decrease is [(206−24)/206]×100=88%

Thus, by including the competitive, non-labeled probe, the sample signal observed using a fully labeled set of capture probes can be confirmed to be true positive signal due to the present of the targeted sequence and not due to a false signal arising from non-specific retention or adsorption.

It is also possible to achieve this competitive effect by using a set of non-labeled reporter probes as well.

All U.S. patents mentioned in this specification are herein incorporated by reference to the same extent as if each individual U.S. patent was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of detecting a target nucleic acid in a sample, said method comprising the steps of:

a) hybridizing a target nucleic acid to a crosslinkable probe, said crosslinkable probe comprising:

i) a polynucleotide having a sequence complementary to that of said target nucleic acid;

ii) a crosslinking moiety comprising a non-nucleosidic coumarin derivative incorporated into the backbone of said polynucleotide such that it replaces one or more nucleotides otherwise complementary to said target nucleic acid, wherein said coumain derivative is linked to a (poly)hydroxy hydrocarbon backbone moiety other than ribose or deoxyribose; and iii) optionally at least one label;

b) activating said crosslinking moiety, whereby a covalent crosslink occurs between said probe and said target nucleic acid; and c) detecting the presence of a crosslinked nucleic acid pair as indicative of the presence of said target sequence in said sample.

2. The method of claim 1 wherein the target nucleic acid is from a microorganism selected from the group consisting of Chlamydia, Neisseria, Mycobacterium, Mycoplasma, Legionella and Listeria monocytogenes.

3. The method of claim 1 wherein the target nucleic acid is from a microorganism selected from the group consisting of *Haemophilus ducreyi, Treponema pallidum, Helicobacter pylori, Pneumocystis carinii, Borrelia burgdorferi*, Salmonella, HIV I and II, HTLV-II, Hepatitis A, B, C, and D, Cytomegalovirus, human Papillomavirus, Respiratory syncytial virus, Epstein-Barr virus, Dengue virus, Eastern and Western Encephalitus viruses, Ebola virus, and Lassa virus.

4. The method of claim 1, wherein the target nucleic acid is selected from the group consisting of the TEM-1 gene (β-lactamase) in Enterobacteriaceae; the TEM-1 gene in penicillinase producing *N. gonorrhoeae* (PPNG); the gene conferring aminoglycoside antibiotic resistance; the gene conferring erythromycin resistance; the gene conferring rifampin resistance and the gene conferring vancomycin resistance.

5. The method of claim 1 wherein the target nucleic acid is selected from the group consisting of fetal DNA, genes indicating sex of a fetus, the factor V gene, the factor V gene having the Leiden mutation, the hemochromatosis gene, the factor II gene and a gene known to be unique to human chromosome 21.

6. The method of claim 1 wherein said crosslinkable probe further comprises at least one label.

7. The method of claim 1, wherein said label is selected from the group consisting of an antibody ligand, a lectin-binding sugar and biotin.

8. The method of claim 1, wherein said label is selected from the group consisting of a chemiluminescer, a radiolabel and a fluorophore.

9. The method of claim 6 wherein said label is an antigen.

10. The method of claim 1 further comprising the step of:
d) isolating said crosslinked nucleic acid pair.

11. The method of claim 1 wherein said target nucleic acid in a sample is genomic DNA.

12. The method of claim 1 wherein said target nucleic acid in a sample is genomic DNA derived from whole blood.

13. A method according to claim 1 wherein multiple samples are assayed for one or more target nucleic acids in an automated system.

14. A kit including components for detecting a target nucleic acid in a sample, said kit comprising:
a) a crosslinkable probe comprising:
   i) a polynucleotide having a sequence complementary to that of said target and capable of hybridizing with said target nucleic acid;
   ii) a crosslinking moiety comprising a non-nucleosidic coumarin derivative incorporated into the backbone of said polynucleotide such that it replaces one or more nucleotides otherwise complementary to said target nucleic acid, wherein said coumarin derivative is linked to a (poly)hydroxy hydrocarbon backbone moiety other than ribose or deoxyribose; and
   iii) optionally at least one label; and
b) a control.

15. A kit according to claim 14 wherein said crosslinkable probe is a first crosslinkable probe, and wherein said kit further comprises at least one second crosslinkable probe, said second crosslinkable probe comprising:
   i) a polynucleotide having a sequence complementary to that of said target nucleic acid;
   ii) a crosslinking moiety comprising a non-nucleosidic coumarin derivative incorporated into the backbone of said polynucleotide such that it replaces one or more nucleotides otherwise complementary to said target nucleic acid, wherein said coumarin derivative is linked to a (poly)hydroxy hydrocarbon backbone moiety other than ribose or deoxyribose; and
   iii) optionally at least one label.

16. A kit according to claim 15 wherein each of said first and second crosslinkable probes are characterized by having a label, wherein one of said labels is a member of a specific binding pair, and one of said labels provides a detectable signal.

17. The kit of claim 14 wherein said control is a purified plasmid containing the nucleic acid sequence to be detected.

18. The kit of claim 14 wherein said control is an amplicon of the region of the target nucleic acid to be detected.

19. A method of detecting a target nucleic acid in a sample, said method comprising the steps of:
a) hybridizing a target nucleic acid to at least a first and a second crosslinkable probe, said crosslinkable probes comprising:
   i) a polynucleotide having a sequence complementary to that of said target nucleic acid;
   ii) a crosslinking moiety comprising a non-nucleosidic coumarin derivative incorporated into the backbone of said polynucleotide such that it replaces one or more nucleotides otherwise complementary to said target nucleic acid, wherein said coumarin derivative is linked to a (poly)hydroxy hydrocarbon backbone moiety other than ribose or deoxyribose; and
   iii) optionally at least one label;
b) activating said crosslinking moiety, whereby a covalent crosslink occurs between said first and second crosslinkable probes and said target nucleic acid; and
c) detecting the presence of a crosslinked nucleic acid pair as indicative of the presence of said target sequence in said sample.

20. The method of claim 19 wherein at least one of said first or second crosslinkable probes is characterized by having at least one label.

21. The method of claim 20, wherein said label is selected from the group consisting of an antibody ligand, a lectin-binding sugar and biotin.

22. The method of claim 20, wherein said label is selected from the group consisting of a chemiluminescer, a radiolabel and a fluorophore.

23. The method of claim 20, wherein said label is an antigen.

24. The method of claim 19, wherein each of said first and second crosslinkable probes are characterized by having a label, wherein one of said labels is a member of a specific binding pair, and one of said labels provides a detectable signal.

* * * * *